(12) United States Patent
Dalal et al.

(10) Patent No.: US 11,446,186 B2
(45) Date of Patent: Sep. 20, 2022

(54) ABSORBENT ARTICLE WITH EAR PORTION

(71) Applicant: The Procter & Gamble Company, Cincinnati, OH (US)

(72) Inventors: Urmish Popatlal Dalal, Milford, OH (US); Todd Douglas Lenser, Liberty Township, OH (US); Uwe Schneider, Cincinnati, OH (US); Todd Joseph Statt, Kings Mill, OH (US); Joerg Mueller, Karben (DE); Melanie Acevedo, Finneytown, OH (US); Hiroshi Nakahata, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 151 days.

(21) Appl. No.: 15/674,561

(22) Filed: Aug. 11, 2017

(65) Prior Publication Data

US 2018/0042785 A1 Feb. 15, 2018

Related U.S. Application Data

(60) Provisional application No. 62/419,518, filed on Nov. 9, 2016, provisional application No. 62/374,286, filed on Aug. 12, 2016.

(51) Int. Cl.
*A61F 13/49* (2006.01)
*A61F 13/56* (2006.01)
(Continued)

(52) U.S. Cl.
CPC .. *A61F 13/49012* (2013.01); *A61F 13/15203* (2013.01); *A61F 13/493* (2013.01);
(Continued)

(58) Field of Classification Search
CPC .. A61F 13/49012; A61F 13/493; A61F 13/84; A61F 13/15203; A61F 13/49015;
(Continued)

(56) References Cited

U.S. PATENT DOCUMENTS 3,113,225 A 12/1963 Claus
3,338,992 A 8/1967 Allison
(Continued)

FOREIGN PATENT DOCUMENTS

CN 104582945 A 4/2015
CN 104703567 A 6/2015
(Continued)

OTHER PUBLICATIONS

International Search Report, PCT/US2017/046398, dated Sep. 28, 2017, 13 pages.
(Continued)

*Primary Examiner* — Tatyana Zalukaeva
*Assistant Examiner* — Meagan Ngo
(74) *Attorney, Agent, or Firm* — Sarah M. DeCristofaro

(57) ABSTRACT

An absorbent article includes a first waist region, a second waist region and a crotch region disposed between the first and second waist regions; and a chassis comprising a topsheet, a backsheet and an absorbent core disposed between the topsheet and the backsheet. The absorbent article also includes an ear disposed in one of the waist regions. The ear includes a laminate having a first nonwoven and a second nonwoven and an elastomeric material sandwiched between said first and second nonwovens in an elasticized region. The laminate also includes a first bonding region comprising a first plurality of ultrasonic bonds having a first bond density, and a second bonding region comprising
(Continued)

a second plurality of ultrasonic bonds having a second bond density. The first bond density is greater than the second bond density.

13 Claims, 7 Drawing Sheets

(51) Int. Cl.
*A61F 13/493* (2006.01)
*A61F 13/84* (2006.01)
*A61F 13/15* (2006.01)

(52) U.S. Cl.
CPC ........ *A61F 13/49015* (2013.01); *A61F 13/56* (2013.01); *A61F 13/5633* (2013.01); *A61F 13/84* (2013.01); *A61F 2013/15357* (2013.01); *A61F 2013/15406* (2013.01); *A61F 2013/8497* (2013.01)

(58) Field of Classification Search
CPC .... A61F 2013/8497; A61F 2013/15357; A61F 2013/15406; A61F 13/56; A61F 13/5633; A61F 2013/49047; A61F 2013/586; A61F 13/5622; A61F 13/5616; A61F 13/58; A61F 2013/587; A61F 2013/588
See application file for complete search history.

(56) References Cited

U.S. PATENT DOCUMENTS

| | | |
|---|---|---|
| 3,562,041 A | 2/1971 | Robertson |
| 3,566,726 A | 3/1971 | Politis |
| 3,692,613 A | 9/1972 | Pederson |
| 3,733,238 A | 5/1973 | Long |
| 3,802,817 A | 4/1974 | Matsuki |
| 3,848,594 A | 11/1974 | Buell |
| 3,849,241 A | 11/1974 | Butin |
| 3,860,003 A | 1/1975 | Buell |
| 3,911,173 A | 10/1975 | Sprague, Jr. |
| 3,929,135 A | 12/1975 | Thompson |
| 4,116,892 A | 9/1978 | Schwarz |
| 4,324,314 A | 4/1982 | Beach et al. |
| 4,405,297 A | 9/1983 | Appel |
| 4,463,045 A | 7/1984 | Ahr et al. |
| 4,573,986 A | 3/1986 | Minetola et al. |
| 4,610,678 A | 9/1986 | Weisman et al. |
| 4,629,643 A | 12/1986 | Curro |
| 4,634,440 A | 1/1987 | Widlund |
| 4,662,875 A | 5/1987 | Hirotsu et al. |
| 4,673,402 A | 6/1987 | Weisman et al. |
| 4,780,352 A | 10/1988 | Palumbo |
| 4,785,996 A | 11/1988 | Ziecker |
| 4,834,735 A | 5/1989 | Alemany et al. |
| 4,834,741 A | 5/1989 | Sabee |
| 4,842,666 A | 6/1989 | Werenicz |
| 4,846,815 A | 7/1989 | Molloy |
| 4,854,984 A | 8/1989 | Ball |
| 4,888,231 A | 12/1989 | Angstadt |
| 4,892,536 A | 1/1990 | DesMarais et al. |
| 4,894,060 A | 1/1990 | Nestegard |
| 4,919,738 A | 4/1990 | Ball |
| 4,940,464 A | 7/1990 | Van Gompel et al. |
| 4,946,527 A | 8/1990 | Battrell |
| 4,990,147 A | 2/1991 | Freeland |
| 5,006,394 A | 4/1991 | Baird |
| 5,037,416 A | 8/1991 | Allen et al. |
| 5,092,861 A | 3/1992 | Nomura |
| 5,137,537 A | 8/1992 | Herron et al. |
| 5,143,679 A | 9/1992 | Weber |
| 5,147,345 A | 9/1992 | Young et al. |
| 5,149,720 A | 9/1992 | Desmarais |
| 5,151,092 A | 9/1992 | Buell et al. |
| 5,156,793 A | 10/1992 | Buell |
| 5,167,897 A | 12/1992 | Weber et al. |
| 5,221,274 A | 6/1993 | Buell et al. |
| 5,242,436 A | 9/1993 | Weil |
| 5,246,433 A | 9/1993 | Hasse |
| 5,260,345 A | 11/1993 | DesMarais et al. |
| 5,266,392 A | 11/1993 | Land |
| 5,269,775 A | 12/1993 | Freeland et al. |
| 5,342,338 A | 8/1994 | Roe |
| 5,360,420 A | 11/1994 | Cook et al. |
| 5,382,400 A | 1/1995 | Pike |
| 5,387,207 A | 2/1995 | Dyer et al. |
| 5,397,316 A | 3/1995 | Lavon et al. |
| 5,418,045 A | 5/1995 | Pike |
| 5,422,172 A | 6/1995 | Wu |
| 5,433,715 A | 7/1995 | Tanzer et al. |
| 5,518,801 A | 5/1996 | Chappell et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,591,155 A | 1/1997 | Nishikawa |
| 5,599,335 A | 2/1997 | Goldman et al. |
| 5,607,414 A | 3/1997 | Richards et al. |
| 5,607,760 A | 3/1997 | Roe |
| 5,609,587 A | 3/1997 | Roe |
| 5,622,772 A | 4/1997 | Stokes |
| 5,628,097 A | 5/1997 | Benson |
| 5,635,191 A | 6/1997 | Roe et al. |
| 5,643,588 A | 7/1997 | Roe et al. |
| 5,658,639 A | 8/1997 | Curro et al. |
| 5,665,300 A | 9/1997 | Brignola |
| 5,674,216 A | 10/1997 | Buell et al. |
| 5,700,254 A | 12/1997 | McDowall et al. |
| 5,702,551 A | 12/1997 | Huber et al. |
| 5,707,468 A | 1/1998 | Arnold |
| 5,817,199 A | 10/1998 | Brennecke et al. |
| 5,827,909 A | 10/1998 | Desmarais |
| 5,865,823 A | 2/1999 | Curro |
| 5,897,545 A | 4/1999 | Kline |
| 5,916,661 A | 6/1999 | Benson et al. |
| 5,957,908 A | 9/1999 | Kline |
| 5,968,025 A | 10/1999 | Roe |
| 5,972,806 A | 10/1999 | Weinberger |
| 5,993,432 A | 11/1999 | Lodge et al. |
| 6,004,306 A | 12/1999 | Robles et al. |
| 6,030,373 A | 2/2000 | Vangompel |
| 6,036,796 A | 3/2000 | Halbert |
| 6,096,668 A | 8/2000 | Abuto |
| 6,107,537 A | 8/2000 | Elder et al. |
| 6,118,041 A | 9/2000 | Roe et al. |
| 6,120,487 A | 9/2000 | Ashton |
| 6,120,489 A | 9/2000 | Johnson |
| 6,123,792 A | 9/2000 | Samida |
| 6,140,551 A * | 10/2000 | Niemeyer ......... A61F 13/15203 604/367 |
| 6,153,209 A | 11/2000 | Vega et al. |
| 6,169,151 B1 | 1/2001 | Waymouth |
| 6,255,236 B1 | 7/2001 | Cree |
| 6,369,121 B1 | 4/2002 | Catalfamo |
| 6,410,129 B2 | 6/2002 | Zhang et al. |
| 6,426,444 B2 | 7/2002 | Roe et al. |
| 6,432,098 B1 | 8/2002 | Kline et al. |
| 6,454,989 B1 | 9/2002 | Neely |
| 6,458,447 B1 | 10/2002 | Cabell |
| 6,465,073 B1 | 10/2002 | Morman |
| 6,472,045 B1 | 10/2002 | Morman |
| 6,472,084 B1 | 10/2002 | Middlesworth |
| 6,475,600 B1 | 11/2002 | Morman |
| 6,498,284 B1 | 12/2002 | Roe |
| 6,508,641 B1 | 1/2003 | Kubik |
| 6,513,221 B2 | 2/2003 | Vogt |
| 6,518,378 B2 | 2/2003 | Waymouth |
| 6,534,149 B1 | 3/2003 | Daley et al. |
| 6,540,854 B2 | 4/2003 | Couillard |
| 6,555,643 B1 | 4/2003 | Rieger |
| 6,559,262 B1 | 5/2003 | Waymouth |
| 6,572,595 B1 | 6/2003 | Klemp et al. |
| 6,572,598 B1 | 6/2003 | Ashton |
| 6,586,652 B1 | 7/2003 | Roe et al. |

(56) References Cited

U.S. PATENT DOCUMENTS

| | | |
|---|---|---|
| 6,610,390 B1 | 8/2003 | Kauschke |
| 6,617,016 B2 | 9/2003 | Zhang et al. |
| 6,627,564 B1 | 9/2003 | Morman |
| 6,627,787 B1 | 9/2003 | Roe et al. |
| 6,632,386 B2 | 10/2003 | Shelley |
| 6,645,330 B2 | 11/2003 | Pargass |
| 6,645,569 B2 | 11/2003 | Cramer et al. |
| 6,649,001 B2 | 11/2003 | Heden |
| 6,677,258 B2 | 1/2004 | Carroll et al. |
| 6,692,477 B2 | 2/2004 | Gibbs |
| 6,713,159 B1 * | 3/2004 | Blenke ............... A61F 13/496 |
| | | 428/195.1 |
| 6,758,925 B1 | 7/2004 | Stegelmann |
| 6,767,420 B2 | 7/2004 | Stegelmann |
| 6,818,083 B2 | 11/2004 | Mcamish et al. |
| 6,825,393 B2 | 11/2004 | Roe et al. |
| 6,830,800 B2 | 12/2004 | Curro |
| 6,843,134 B2 | 1/2005 | Anderson |
| 6,849,142 B1 | 2/2005 | Goulait |
| 6,861,571 B1 | 3/2005 | Roe et al. |
| 6,863,933 B2 | 3/2005 | Cramer et al. |
| 6,878,433 B2 | 4/2005 | Curro et al. |
| 6,974,514 B2 | 12/2005 | Hamulski |
| 7,056,404 B2 | 6/2006 | McFall et al. |
| 7,062,983 B2 | 6/2006 | Anderson |
| 7,108,759 B2 | 9/2006 | You |
| 7,112,621 B2 | 9/2006 | Rohrbaugh et al. |
| 7,270,861 B2 | 9/2007 | Broering |
| 7,291,239 B2 | 11/2007 | Polanco |
| 7,435,243 B2 | 10/2008 | Miyamoto |
| 7,531,233 B2 | 5/2009 | Kling |
| 7,569,039 B2 | 8/2009 | Matsuda |
| 7,572,249 B2 | 8/2009 | Betts |
| 7,582,075 B2 | 9/2009 | Betts |
| 7,625,363 B2 | 12/2009 | Yoshimasa |
| 7,741,235 B2 | 6/2010 | Hashimoto |
| 7,803,244 B2 | 9/2010 | Siqueira |
| 7,806,883 B2 | 10/2010 | Fossum et al. |
| 7,819,853 B2 | 10/2010 | Desai et al. |
| 7,824,594 B2 | 11/2010 | Qureshi |
| 7,870,651 B2 | 1/2011 | Middlesworth |
| 7,896,641 B2 | 3/2011 | Qureshi |
| 7,917,985 B2 | 4/2011 | Dorsey |
| 7,931,632 B2 | 4/2011 | Betts |
| 7,954,213 B2 | 6/2011 | Mizutani |
| 7,998,127 B2 | 8/2011 | Betts |
| 8,062,279 B2 | 11/2011 | Miyamoto |
| 8,062,572 B2 | 11/2011 | Qureshi |
| 8,092,438 B2 | 1/2012 | Betts |
| 8,118,801 B2 | 2/2012 | Macura |
| 8,158,043 B2 | 4/2012 | Gibson |
| 8,172,971 B2 | 5/2012 | Yamamoto |
| 8,186,296 B2 | 5/2012 | Brown et al. |
| 8,361,913 B2 | 1/2013 | Siqueira |
| 8,450,557 B2 | 5/2013 | Nishitani |
| 8,454,571 B2 | 6/2013 | Rezai et al. |
| 8,480,642 B2 | 7/2013 | Betts |
| 8,491,557 B2 | 7/2013 | Kline et al. |
| 8,491,742 B2 | 7/2013 | Waas |
| 8,496,775 B2 | 7/2013 | Deng |
| 8,502,013 B2 | 8/2013 | Zhao |
| 8,518,004 B2 | 8/2013 | Betts |
| 8,585,666 B2 | 11/2013 | Weisman et al. |
| 8,618,350 B2 | 12/2013 | Mansfield |
| 8,679,391 B2 | 3/2014 | Odonnell |
| 8,690,852 B2 | 4/2014 | Macura et al. |
| 8,697,938 B2 | 4/2014 | Roe et al. |
| 8,709,579 B2 | 4/2014 | Hoenigmann et al. |
| 8,728,051 B2 | 5/2014 | Lu |
| 8,741,083 B2 | 6/2014 | Wennerback |
| 8,776,856 B2 | 7/2014 | Yamamoto |
| 8,795,809 B2 | 8/2014 | Manfield |
| 8,858,523 B2 | 10/2014 | Sauer et al. |
| 8,939,957 B2 | 1/2015 | Ray et al. |
| 8,940,116 B2 | 1/2015 | Giigenbach |
| 9,102,132 B2 | 8/2015 | Wennerbck |
| 9,211,221 B2 | 12/2015 | Macura et al. |
| 9,301,889 B2 | 4/2016 | Miyamoto |
| 9,358,161 B2 | 6/2016 | Lawson et al. |
| 9,434,143 B2 | 9/2016 | Sablone |
| 9,498,941 B2 | 11/2016 | Sablone |
| 9,533,067 B2 | 1/2017 | Schoenbeck et al. |
| 9,687,580 B2 | 6/2017 | Schonbeck |
| 9,724,248 B2 | 8/2017 | Hughes |
| 9,821,542 B2 | 11/2017 | Bruce |
| 10,524,964 B2 | 1/2020 | Sauer |
| 10,568,775 B2 | 2/2020 | Leaser |
| 10,568,776 B2 | 2/2020 | Lenser |
| 10,575,993 B2 | 3/2020 | Lenser |
| 10,588,789 B2 | 3/2020 | Surushe |
| 10,617,573 B2 | 4/2020 | Koshijima |
| 10,966,876 B2 | 4/2021 | Lenser et al. |
| 2001/0018579 A1 | 8/2001 | Klemp |
| 2001/0024940 A1 | 9/2001 | Cook et al. |
| 2002/0095129 A1 | 7/2002 | Friderich |
| 2002/0188268 A1 * | 12/2002 | Kline ............... A61F 13/622 |
| | | 604/385.3 |
| 2003/0021951 A1 | 1/2003 | Desai |
| 2003/0105446 A1 | 6/2003 | Hutson |
| 2003/0109843 A1 | 6/2003 | Gibbs |
| 2003/0109844 A1 * | 6/2003 | Gibbs ............... A61F 13/5622 |
| | | 604/389 |
| 2003/0120240 A1 | 6/2003 | Buell |
| 2003/0124310 A1 | 7/2003 | Ellis |
| 2003/0148684 A1 | 8/2003 | Cramer et al. |
| 2003/0233082 A1 | 12/2003 | Kline |
| 2004/0091693 A1 | 5/2004 | Thomas |
| 2004/0102125 A1 | 5/2004 | Morman |
| 2004/0112509 A1 | 6/2004 | Morman |
| 2004/0121690 A1 | 6/2004 | Mleziva |
| 2004/0182499 A1 | 9/2004 | Collier |
| 2004/0224132 A1 | 11/2004 | Roe |
| 2005/0008839 A1 | 1/2005 | Cramer et al. |
| 2005/0065487 A1 | 3/2005 | Graef |
| 2005/0107764 A1 | 5/2005 | Matsuda et al. |
| 2005/0154362 A1 | 7/2005 | Warren |
| 2005/0245162 A1 | 11/2005 | Mccormack |
| 2005/0287892 A1 | 12/2005 | Fouse |
| 2006/0062963 A1 | 3/2006 | Middiesworth |
| 2006/0089616 A1 | 4/2006 | Belau et al. |
| 2006/0135024 A1 | 6/2006 | Thomas |
| 2006/0148361 A1 | 7/2006 | Mccormack |
| 2006/0149209 A1 | 7/2006 | Malchow |
| 2006/0287637 A1 | 12/2006 | Lam |
| 2007/0105472 A1 | 5/2007 | Marche |
| 2007/0123124 A1 | 5/2007 | Middlesworth |
| 2007/0142798 A1 | 6/2007 | Goodlander |
| 2007/0142806 A1 | 6/2007 | Roe et al. |
| 2007/0142825 A1 | 6/2007 | Prisco |
| 2007/0143972 A1 | 6/2007 | Kline |
| 2007/0202767 A1 | 8/2007 | Anderson |
| 2007/0219521 A1 | 9/2007 | Hird |
| 2007/0249254 A1 | 10/2007 | Mansfield |
| 2007/0254176 A1 | 11/2007 | Patel |
| 2007/0254547 A1 | 11/2007 | Ducauchuis |
| 2007/0287983 A1 | 12/2007 | Lodge |
| 2008/0003910 A1 | 1/2008 | Hughes |
| 2008/0003911 A1 | 1/2008 | Sabbagh |
| 2008/0051748 A1 | 2/2008 | Black |
| 2008/0076315 A1 | 3/2008 | Mccormack |
| 2008/0119102 A1 | 5/2008 | Hughes |
| 2008/0147031 A1 | 6/2008 | Long |
| 2008/0241476 A1 | 10/2008 | Olguin |
| 2008/0305298 A1 | 12/2008 | Lakshmi |
| 2008/0312622 A1 | 12/2008 | Hundorf |
| 2009/0035527 A1 | 2/2009 | Kobayashi |
| 2009/0069772 A1 | 3/2009 | Sauer |
| 2009/0069778 A1 | 3/2009 | Sauer |
| 2009/0191779 A1 | 7/2009 | Cree |
| 2009/0240222 A1 | 9/2009 | Tomoko |
| 2009/0258210 A1 | 10/2009 | Muslet et al. |
| 2009/0275909 A1 | 11/2009 | Sakaguchi |
| 2009/0292266 A1 | 11/2009 | Bäck |
| 2009/0294044 A1 | 12/2009 | Gill |

(56) References Cited

U.S. PATENT DOCUMENTS

| | | |
|---|---|---|
| 2009/0299318 A1 | 12/2009 | Faulks |
| 2009/0299322 A1 | 12/2009 | Faulks |
| 2009/0325447 A1 | 12/2009 | Austin |
| 2009/0325448 A1 | 12/2009 | Welch |
| 2010/0062231 A1 | 3/2010 | Abed |
| 2010/0076390 A1 | 3/2010 | Norrby |
| 2010/0090363 A1 | 4/2010 | Larsen |
| 2010/0104830 A1 | 4/2010 | Jaeger |
| 2010/0112313 A1 | 5/2010 | Nakakado |
| 2010/0168704 A1 | 7/2010 | Thomas |
| 2010/0262105 A1 | 10/2010 | Turner |
| 2010/0268183 A1 | 10/2010 | Een |
| 2010/0280481 A1 | 11/2010 | Kline |
| 2011/0004176 A1* | 1/2011 | Andersson ............ A61F 13/512 604/378 |
| 2011/0040273 A1 | 2/2011 | Sablone |
| 2011/0046594 A1 | 2/2011 | Sablone |
| 2011/0139657 A1 | 6/2011 | Hird |
| 2011/0139658 A1 | 6/2011 | Hird |
| 2011/0139659 A1 | 6/2011 | Hird |
| 2011/0144610 A1 | 6/2011 | Karison |
| 2011/0152812 A1 | 6/2011 | Hird |
| 2011/0178490 A1 | 7/2011 | Lavon |
| 2011/0196332 A1* | 8/2011 | Cheng ................. A61F 13/4753 604/385.24 |
| 2011/0318987 A1 | 12/2011 | Ooishi |
| 2012/0045620 A1 | 2/2012 | Oba |
| 2012/0055613 A1 | 3/2012 | Baeck |
| 2012/0055615 A1 | 3/2012 | Baeck |
| 2012/0061015 A1 | 3/2012 | Lavon et al. |
| 2012/0061016 A1 | 3/2012 | Lavon et al. |
| 2012/0095429 A1 | 4/2012 | Kobayashi |
| 2012/0100351 A1 | 4/2012 | Covelli |
| 2012/0116342 A1 | 5/2012 | Stjernholm |
| 2012/0141742 A1 | 6/2012 | Yamaguchi |
| 2012/0143165 A1 | 6/2012 | Macura |
| 2012/0168063 A1 | 7/2012 | Beuther |
| 2012/0196091 A1 | 8/2012 | Mizutani |
| 2012/0209230 A1 | 8/2012 | Mansfield |
| 2012/0238980 A1* | 9/2012 | Lam ...................... A61F 13/581 604/369 |
| 2012/0251771 A1 | 10/2012 | Wilson |
| 2012/0277713 A1 | 11/2012 | Raycheck |
| 2012/0316526 A1 | 12/2012 | Rosati et al. |
| 2012/0321839 A1 | 12/2012 | Uematsu |
| 2013/0017370 A1 | 1/2013 | Yamaguchi |
| 2013/0022784 A1 | 1/2013 | Uematsu |
| 2013/0072887 A1 | 3/2013 | Lavon |
| 2013/0082418 A1 | 4/2013 | Curro et al. |
| 2013/0090623 A1 | 4/2013 | Ohashi |
| 2013/0095279 A1 | 4/2013 | Hauschildt |
| 2013/0144245 A1 | 6/2013 | Roe |
| 2013/0158497 A1 | 6/2013 | Yamaguchi |
| 2013/0164480 A1 | 6/2013 | Sakurai |
| 2013/0165883 A1 | 6/2013 | Kimura |
| 2013/0178815 A1 | 7/2013 | Ohashi |
| 2013/0184665 A1 | 7/2013 | Kato |
| 2013/0211356 A1 | 8/2013 | Nishikawa et al. |
| 2013/0213547 A1 | 8/2013 | Schneider |
| 2013/0218116 A1 | 8/2013 | Schneider |
| 2013/0230700 A1 | 9/2013 | Schoenbeck |
| 2013/0236700 A1 | 9/2013 | Yamanaka |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0280481 A1 | 10/2013 | Mitsuno |
| 2013/0284850 A1 | 10/2013 | Leaser |
| 2013/0306226 A1 | 11/2013 | Zink |
| 2014/0018222 A1 | 1/2014 | Sablone |
| 2014/0018759 A1 | 1/2014 | Jayasinghe et al. |
| 2014/0039434 A1 | 2/2014 | Xu |
| 2014/0041786 A1 | 2/2014 | Henke |
| 2014/0135194 A1 | 5/2014 | Sablone |
| 2014/0148774 A1 | 5/2014 | Brown |
| 2014/0163500 A1 | 6/2014 | Roe |
| 2014/0163506 A1 | 6/2014 | Roe |
| 2014/0163511 A1 | 6/2014 | Roe et al. |
| 2014/0234575 A1 | 8/2014 | Mitsuno et al. |
| 2014/0330232 A1* | 11/2014 | Schonbeck ....... A61F 13/49019 604/365 |
| 2014/0377506 A1 | 12/2014 | Eckstein et al. |
| 2014/0377513 A1 | 12/2014 | Galie |
| 2014/0378924 A1 | 12/2014 | Turner |
| 2015/0032078 A1* | 1/2015 | Collins ............... A61F 13/5633 604/391 |
| 2015/0038929 A1 | 2/2015 | Van Malderen |
| 2015/0057630 A1 | 2/2015 | Tange |
| 2015/0126955 A1 | 5/2015 | Sauer et al. |
| 2015/0147530 A1 | 5/2015 | Mitsuno |
| 2015/0147539 A1 | 5/2015 | Thomas |
| 2015/0164699 A1 | 6/2015 | Schmitz |
| 2015/0164705 A1 | 6/2015 | Thomas |
| 2015/0173961 A1 | 6/2015 | Powell et al. |
| 2015/0202091 A1 | 7/2015 | Sablone |
| 2015/0297419 A1 | 10/2015 | Nelson |
| 2015/0297421 A1 | 10/2015 | Nelson |
| 2015/0313774 A1 | 11/2015 | Homoelle |
| 2016/0013614 A1 | 1/2016 | Moto |
| 2016/0136014 A1 | 5/2016 | Arora et al. |
| 2016/0167334 A1 | 6/2016 | Arora |
| 2016/0206485 A1 | 7/2016 | Seitz |
| 2016/0270972 A1 | 9/2016 | Surushe et al. |
| 2016/0324697 A1* | 11/2016 | Schoenbeck ............... B32B 7/05 |
| 2017/0027775 A1 | 2/2017 | Barnes |
| 2017/0056256 A1 | 3/2017 | Smith et al. |
| 2017/0079851 A1 | 3/2017 | Greening, II |
| 2017/0079854 A1 | 3/2017 | Butler |
| 2017/0087029 A1 | 3/2017 | Nelson |
| 2017/0252229 A1 | 9/2017 | Bonelli |
| 2017/0335498 A1 | 11/2017 | Hansen |
| 2018/0014979 A1 | 1/2018 | Fujita |
| 2018/0015709 A1 | 1/2018 | Takeuchi |
| 2018/0042777 A1 | 2/2018 | Dalal |
| 2018/0042778 A1 | 2/2018 | Lenser |
| 2018/0042779 A1 | 2/2018 | Lenser |
| 2018/0042780 A1 | 2/2018 | Lenser |
| 2018/0042784 A1 | 2/2018 | Koshijima |
| 2018/0042786 A1 | 2/2018 | Mueller |
| 2018/0042787 A1 | 2/2018 | Lenser et al. |
| 2018/0271716 A1 | 9/2018 | Dalai |
| 2018/0271717 A1 | 9/2018 | Dria |
| 2018/0281296 A1 | 10/2018 | Uchida |
| 2019/0046363 A1 | 2/2019 | Lenser |
| 2019/0083323 A1 | 3/2019 | Sakai |
| 2019/0110936 A1 | 4/2019 | Becker |
| 2020/0170846 A1 | 6/2020 | Lenser |
| 2020/0179179 A1 | 6/2020 | Lenser |
| 2020/0268563 A1 | 8/2020 | Lenser |
| 2021/0186769 A1 | 6/2021 | Lenser et al. |
| 2021/0186770 A1 | 6/2021 | Lenser et al. |

FOREIGN PATENT DOCUMENTS

| | | |
|---|---|---|
| CN | 104797228 A | 7/2015 |
| CN | 103434239 B | 11/2015 |
| CN | 204909840 U | 12/2015 |
| CN | 104387455 B | 4/2018 |
| EP | 1256594 A1 | 11/2002 |
| EP | 1447066 A1 | 8/2004 |
| EP | 1263580 B1 | 9/2010 |
| EP | 1990188 B1 | 10/2012 |
| EP | 2891480 A1 | 7/2015 |
| EP | 2841364 B1 | 8/2016 |
| EP | 3246443 A1 | 11/2017 |
| EP | 3251644 A1 | 12/2017 |
| EP | 2647360 B1 | 6/2018 |
| EP | 3251642 B1 | 8/2020 |
| JP | 2004223238 A | 8/2004 |
| JP | 2007521036 A | 8/2007 |
| JP | 2011139843 A | 7/2011 |
| JP | 4934835 B2 | 3/2012 |
| JP | 5036641 B2 | 7/2012 |

(56) References Cited

FOREIGN PATENT DOCUMENTS

| | | |
|---|---|---|
| JP | 2012524645 A | 10/2012 |
| JP | 2017065142 A | 4/2017 |
| JP | 6240733 B1 | 11/2017 |
| WO | 9510996 A1 | 4/1995 |
| WO | 9511652 A1 | 5/1995 |
| WO | WO 95/16746 | 6/1995 |
| WO | 9828123 A1 | 7/1998 |
| WO | 2000045763 A1 | 8/2000 |
| WO | 2000059430 A1 | 10/2000 |
| WO | 0073031 A1 | 12/2000 |
| WO | 2002067809 A2 | 9/2002 |
| WO | 2003007864 A1 | 1/2003 |
| WO | WO 2004/017882 | 3/2004 |
| WO | WO 2004/017885 | 3/2004 |
| WO | 2004060652 A1 | 7/2004 |
| WO | WO 2006/124337 | 11/2006 |
| WO | WO 2006/138725 | 12/2006 |
| WO | WO 2007/03 6907 | 4/2007 |
| WO | 2008023291 A3 | 2/2008 |
| WO | 2008156075 A1 | 12/2008 |
| WO | 2009146307 A1 | 12/2009 |
| WO | 2010055699 A1 | 5/2010 |
| WO | 2010118214 A1 | 10/2010 |
| WO | 2010126415 A1 | 11/2010 |
| WO | 2011080643 A2 | 7/2011 |
| WO | 2011125893 A1 | 10/2011 |
| WO | 2012052172 A1 | 4/2012 |
| WO | 2012030571 A3 | 5/2012 |
| WO | WO 2012/112501 | 8/2012 |
| WO | 2012137553 A1 | 10/2012 |
| WO | 2012154318 A1 | 11/2012 |
| WO | 2013018846 A1 | 2/2013 |
| WO | 2013027390 A1 | 2/2013 |
| WO | 2013047890 A1 | 4/2013 |
| WO | 2013132403 A1 | 9/2013 |
| WO | 2013157365 A1 | 10/2013 |
| WO | 2013163141 A1 | 10/2013 |
| WO | 2014011839 A1 | 1/2014 |
| WO | 2015168032 A1 | 11/2015 |
| WO | 2015195467 A1 | 12/2015 |
| WO | 2015195468 A1 | 12/2015 |
| WO | 2016069269 A1 | 5/2016 |
| WO | WO 2016/073713 | 5/2016 |
| WO | 2016109514 A1 | 7/2016 |
| WO | 2018031841 A1 | 2/2018 |
| WO | 2018183315 A1 | 10/2018 |
| WO | 2016121979 A1 | 1/2019 |
| WO | 2019089689 A2 | 5/2019 |

OTHER PUBLICATIONS

All Office Actions, U.S. Appl. No. 15/674,559.
All Office Actions, U.S. Appl. No. 15/674,563.
All Office Actions, U.S. Appl. No. 15/674,566.
All Office Actions, U.S. Appl. No. 15/674,575.
All Office Actions, U.S. Appl. No. 15/674,596.
All Office Actions, U.S. Appl. No. 15/674,625.
All Office Actions, U.S. Appl. No. 15/937,180.
All Office Actions, U.S. Appl. No. 15/937,235.
All Office Actions, U.S. Appl. No. 16/049,977.
All Office Actions, U.S. Appl. No. 16/741,819.
All Office Actions, U.S. Appl. No. 16/748,885.
Case 14424; PCT International Search Report, Appl. No. PCT/US2017/046388, dated Sep. 22, 2017, 15 pages.
Case 14445MQ; International Search Report, Appl. No. PCT/US2017/046397, dated Sep. 28, 2017, 13 pages.
Case 14525; PCT International Search Report and Written Opinion, Appl. No. PCT/US2017/046393, dated Sep. 25, 2017, 16 pages.
Case 14562Q; PCT International Search Report, Appl. No. PCT/US2017/046394, dated Sep. 28, 2017, 15 pages.
Case 14756M; International Search Report and Written Opinion, Appl. No. PCT/US2018/024549, dated May 30, 2018, 13 pages.
Case 14911; PCT International Search Report, Appl. No. PCT/US2017/046395, dated Sep. 20, 2017, 15 pages.
Case 14915Q; EP Application No. 17764961.3, Third Party Observation, dated Aug. 24, 2020, 6 pages.
Case 15168; International Search Report, Appl. No. PCT/US2019/024011, dated Jul. 4, 2019, 14 pages.
EP Application No. 17754982.1, Third Party Observation, dated Jun. 17, 2020, 9 pages.
Extended European Search Report and Search Opinion; Application No. 20183749.9; dated Nov. 9, 2020; 8 pages.
International Search Report and Written Opinion, Application No. PCT/US2017/049026, dated Oct. 19, 2017, 13 pages.
International Search Report and Written Opinion; Application No. PCT/US2020/070219; dated Oct. 1, 2020; 14 pages.
All Office Actions; U.S. Appl. No. 17/195,677, filed Mar. 9, 2021.
All Office Actions; U.S. Appl. No. 16/916,655, filed Jun. 30, 2020.
All Office Actions; U.S. Appl. No. 17/195,679, filed Mar. 9, 2021.
U.S. Appl. No. 16/916,655, filed Jun. 30, 2020, Nelson Edward Greening, II et al.
All Office Actions; U.S. Appl. No. 17/720,363, filed Apr. 14, 2022.
Unpublished U.S. Appl. No. 17/720,363, filed Apr. 14, 2022, to Todd Douglas Lenser.

* cited by examiner

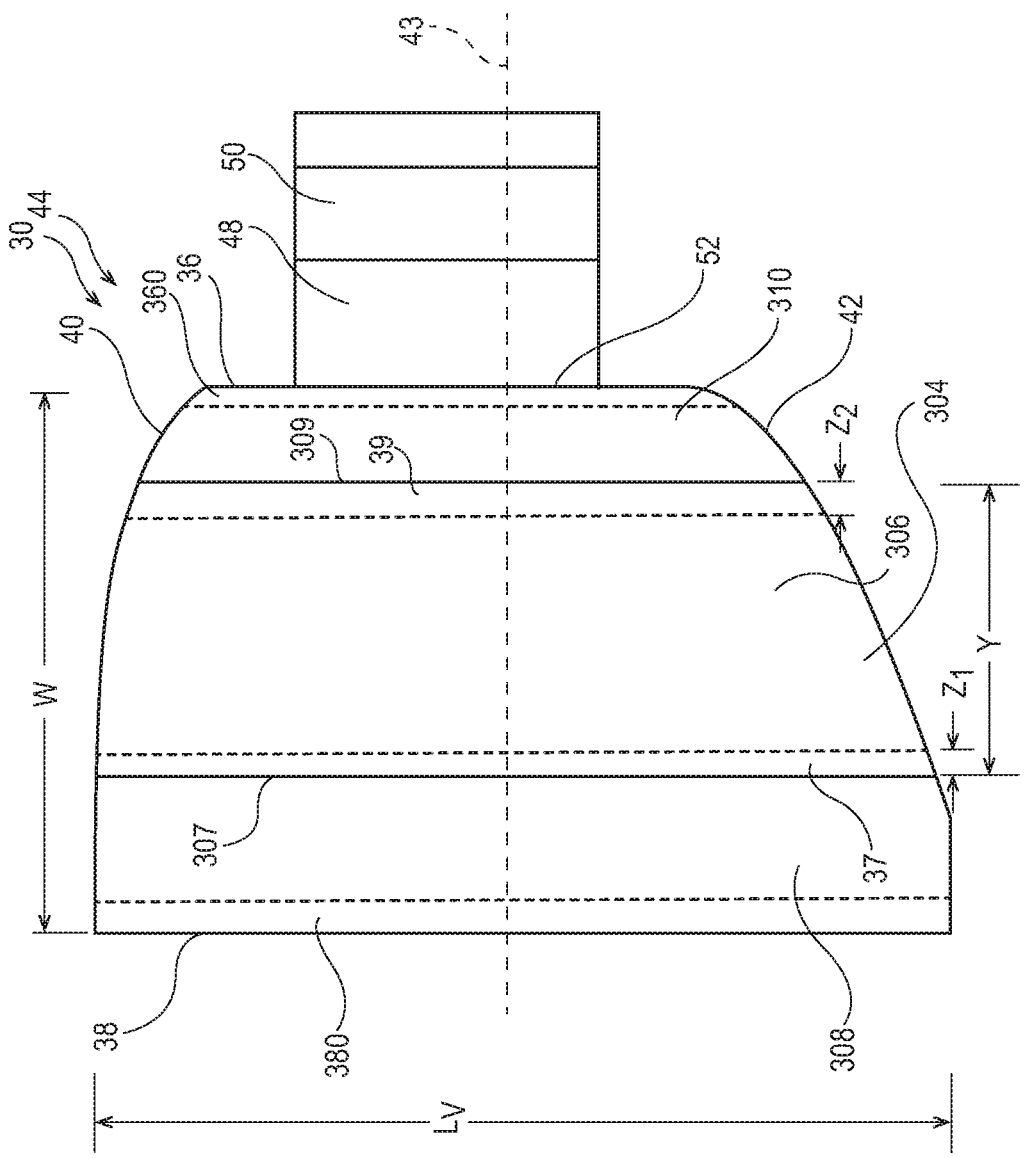

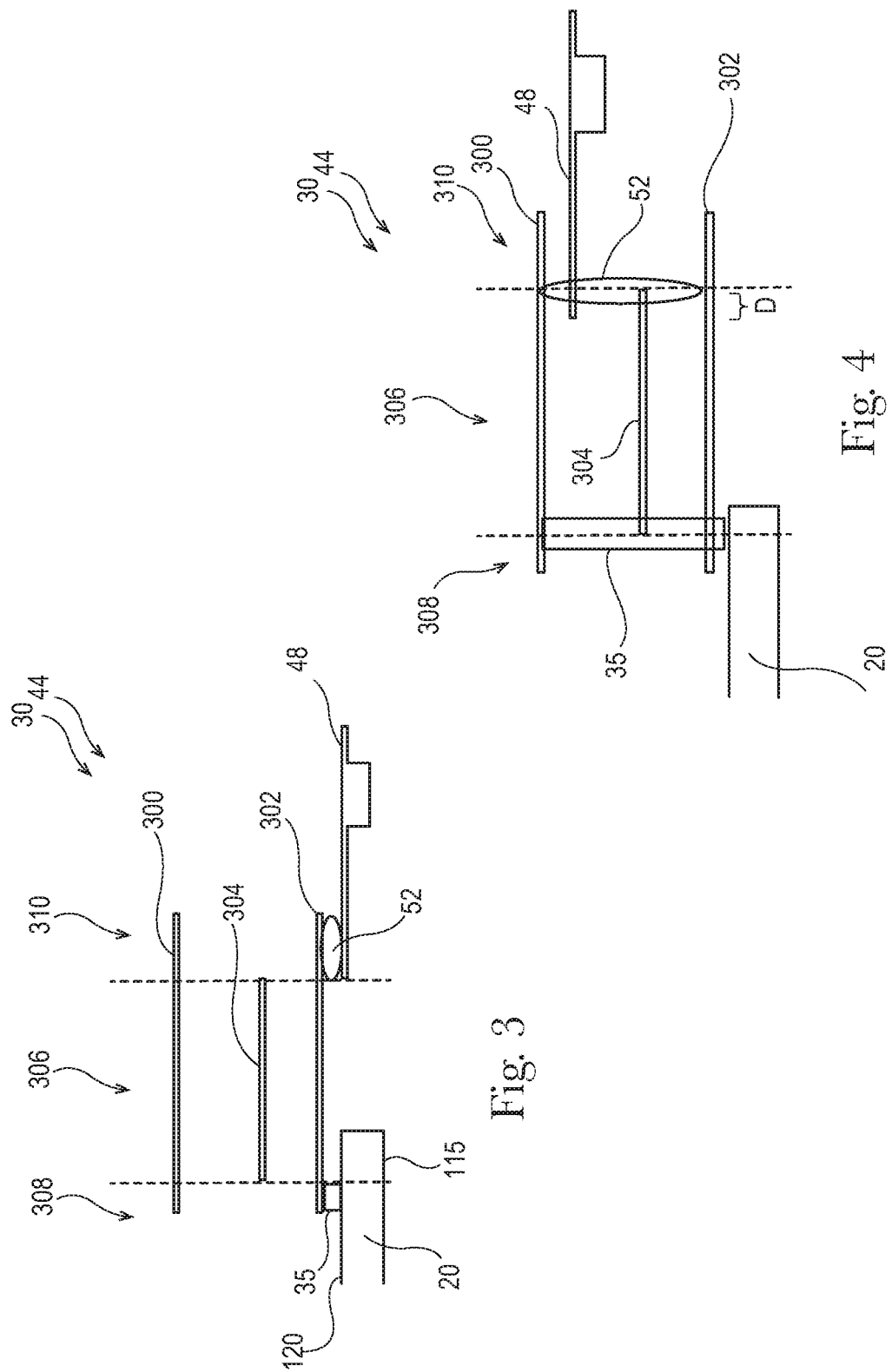

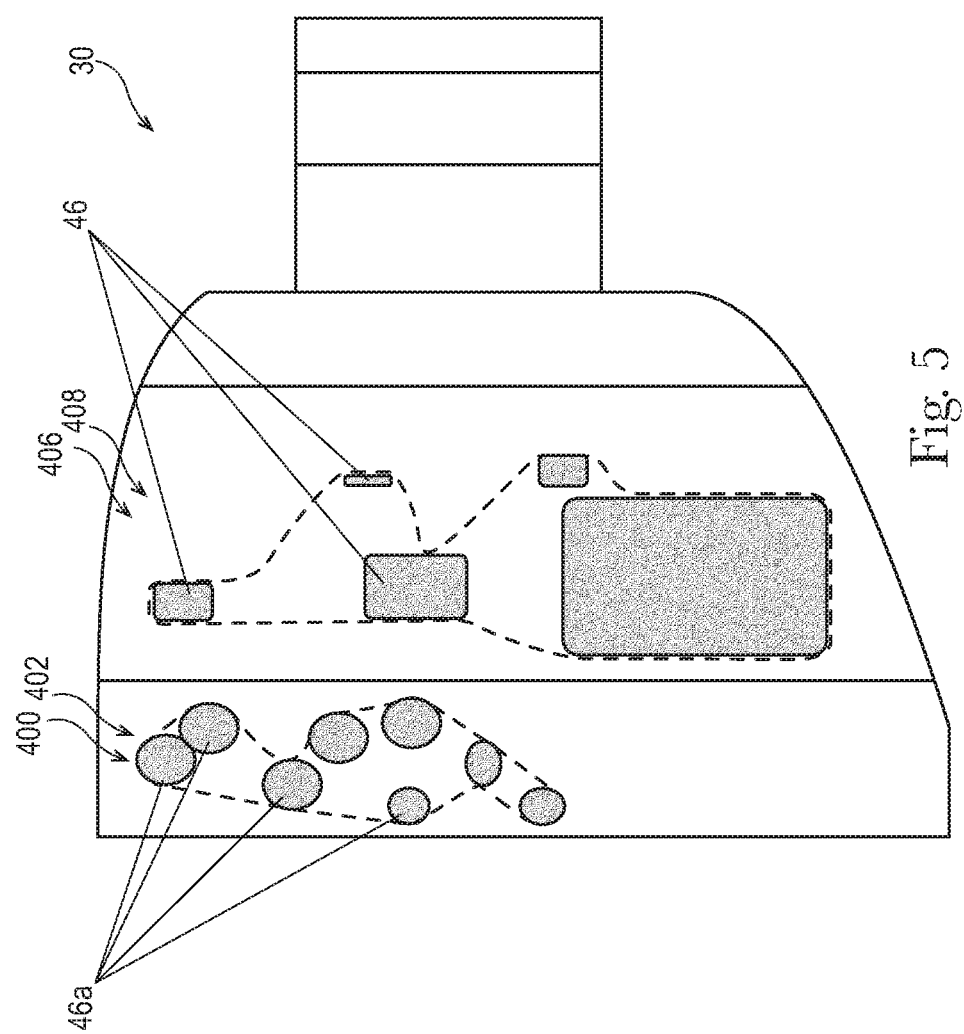

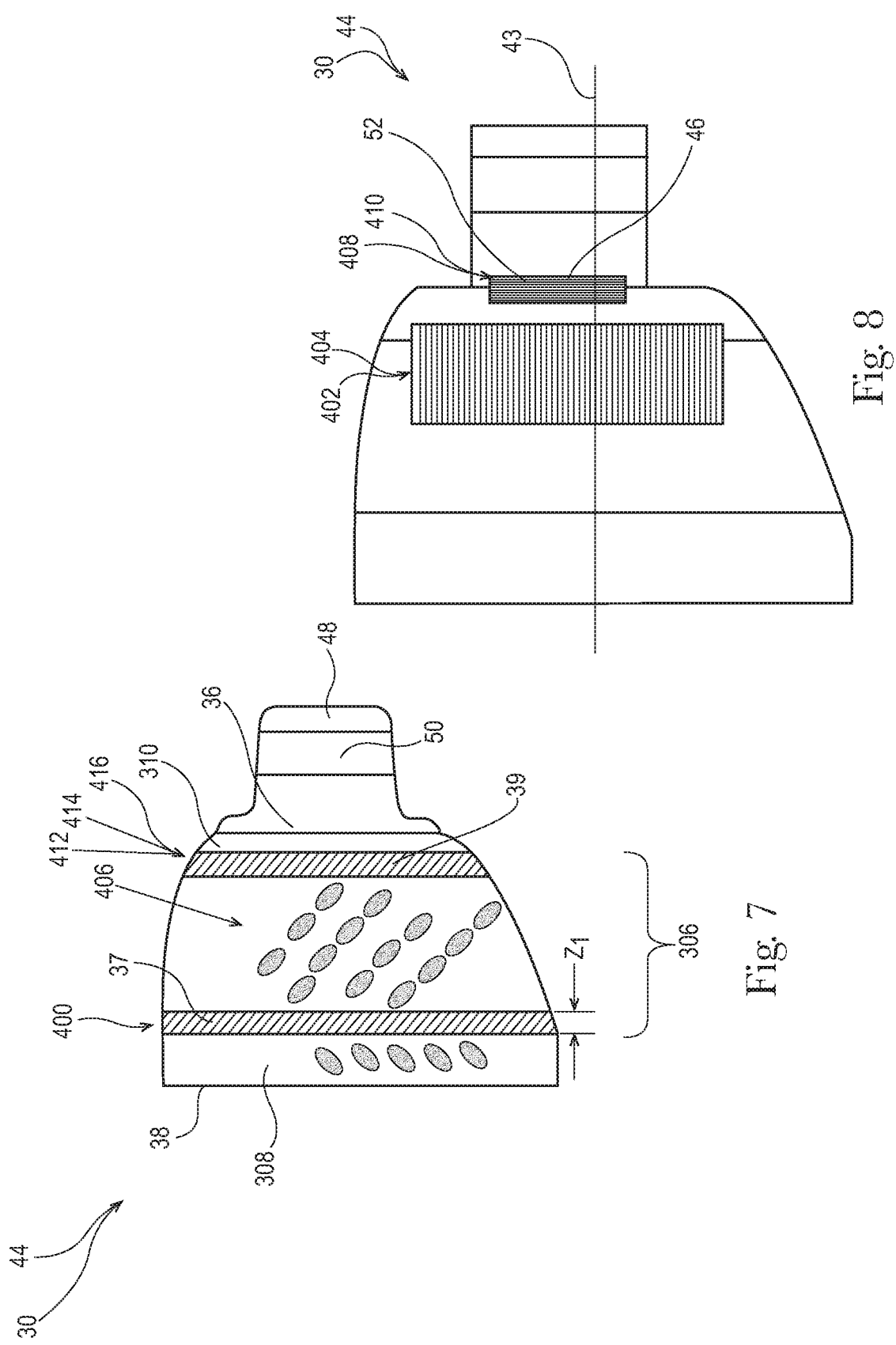

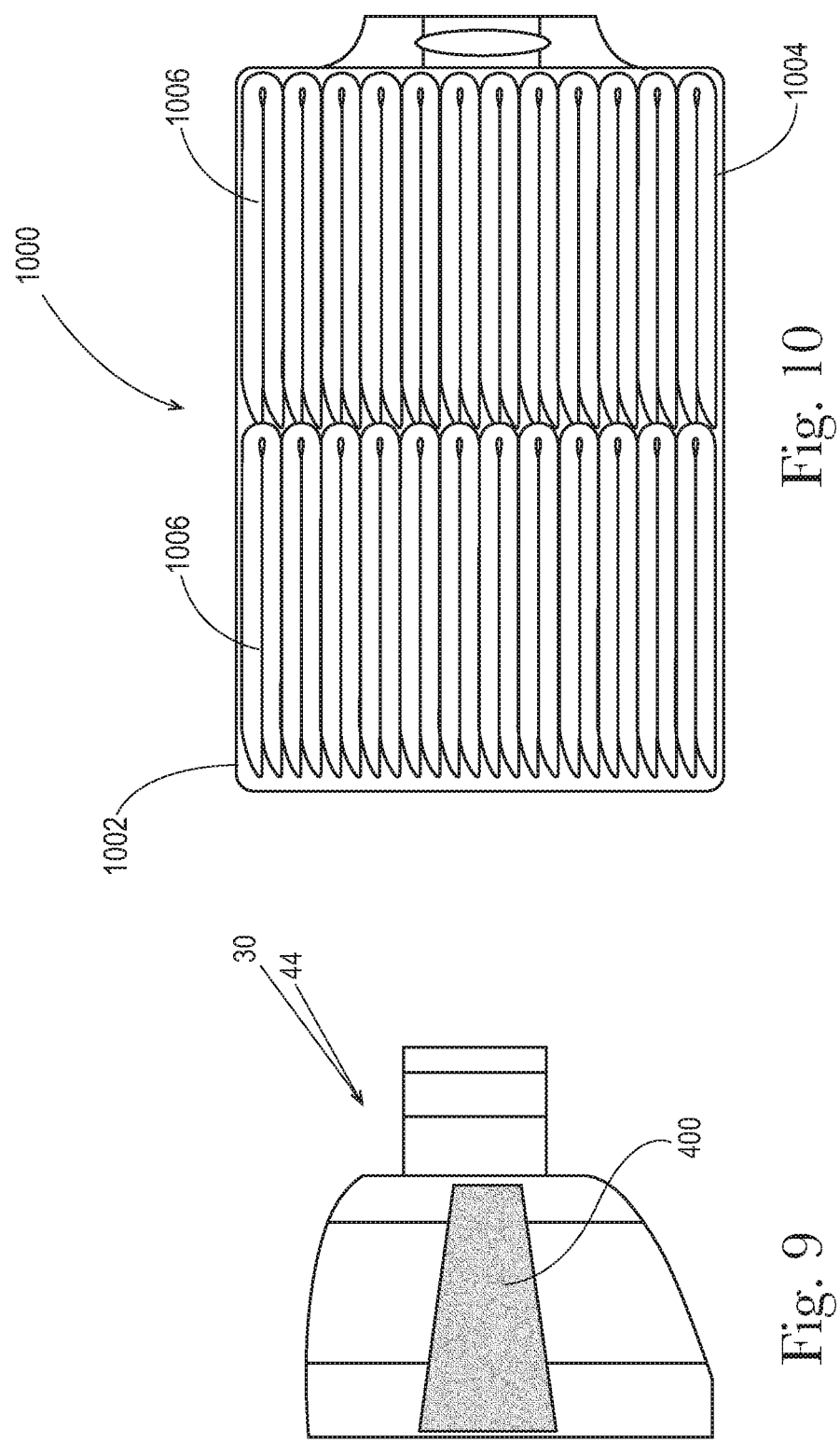

ABSORBENT ARTICLE WITH EAR PORTION

FIELD OF THE INVENTION

The present invention relates to absorbent articles having ear portions, in particular stretchable ears.

BACKGROUND OF THE INVENTION

It has long been known that absorbent articles such as conventional absorbent articles (e.g., diapers, adult incontinence articles, feminine hygiene pads) offer the benefit of receiving and containing urine and/or other bodily exudates (e.g., feces, menses, mixture of feces and urine, mixture of menses and urine, etc.). To effectively contain bodily exudates, the article should provide a snug fit around the waist and legs of a wearer.

Manufacturers often use extensible areas, such as stretch side panels (i.e., ears), within the article to help achieve a snug fit. When worn, the stretch ears extend the article about the hip and waist of the wearer to anchor the product in use while still allowing the wearer to move comfortably. A fastening system is typically joined to the ear to further secure the product about the wearer. Stretch ears are typically laminates of coverstock materials (such as nonwovens) and elastomeric materials.

It has been proposed to create stretch laminates using ultrasonic bonding. In such instance, a stretched elastomeric material is combined with a nonwoven via ultrasonic bonding. After combination, the nonwoven will form corrugations when the laminate is in a relaxed state. These laminates can produce highly stretchable ears (depending on the level of stretch imparted in the elastomeric material) while avoiding the use of glues and mechanical activation. Further, unlike other forms of lamination, the elastomeric material need not extend across the entire width of the laminate. However, ultrasonically bonded ears lack the strength of other ears. During application, if the ears lack necessary strength, the ear itself may break, a fastener may become detached from the ear, and/or the ear may detach from the rest of the article. Such failures render the article itself unusable.

In addition to the need for adequate strength, manufacturers must balance a number of other factors when constructing an ear, including minimal stress concentrations, desired force and stretch profiles, breathability, shape as well as aesthetic appeal. Further, in order to remain competitive in their field, it is important to reduce costs and enhance efficiency during the production process.

Therefore, there is a continued need for stretch ears having desirable stretch balanced with adequate strength, especially thermally (in particular ultrasonically bonded) stretch ears having adequate strength. Further, there is a need for stretch ears having improved breathability while maintaining strength, appropriate stress profiles and/or other desirable properties. There is also a need for stretch ears which provide desired stretch and/or force profiles. In addition, there is a need to provide desired properties and/or customizable profiles with minimal costs and high efficiency.

SUMMARY OF THE INVENTION

In embodiments, an absorbent article includes a first waist region, a second waist region and a crotch region disposed between the first and second waist regions; and a chassis comprising a topsheet, a backsheet and an absorbent core disposed between the topsheet and the backsheet. The absorbent article also includes an ear disposed in one of the waist regions. The ear has a proximate side and a distal side; and an elasticized region. The ear includes a laminate having a first nonwoven and a second nonwoven and an elastomeric material sandwiched between said first and second nonwovens in the elasticized region.

The laminate may include a first bonding region and a second bonding region. The first bonding region may comprise a first plurality of ultrasonic bonds having a first bond density, and the second bonding region may comprise a second plurality of ultrasonic bonds having a second bond density. The first bond density may be greater than the second bond density. In further embodiments, the first bonding region may comprise a first ultrasonic bond pattern and the second bonding region may comprise a second ultrasonic bond pattern. The second ultrasonic bond pattern may differ from the first ultrasonic bond pattern by design elements, average bond spacing, pattern uniformity, bond size, bond shape, bond orientation, aggregate bond area, aggregate bond coverage, aggregate pattern shape and/or combinations thereof.

In certain embodiments, an absorbent article includes a first waist region, a second waist region and a crotch region disposed between the first and second waist regions; and a chassis comprising a topsheet, a backsheet and an absorbent core disposed between the topsheet and the backsheet. The absorbent article also includes an ear disposed in one of the first or second waist regions, wherein the ear is laterally-extensible. The ear has a proximate side and a distal side; an elasticized region; and a laminate. The laminate includes a first nonwoven and a second nonwoven and an elastomeric material sandwiched between said first and second nonwovens in the elasticized region. The laminate also includes a first pattern of ultrasonic bonds. A fastening system may be joined to the ear and may include a fastener pattern of ultrasonic bonds. The first pattern may match the fastener pattern.

In further embodiments, an absorbent article includes a first waist region, a second waist region and a crotch region disposed between the first and second waist regions; and a chassis comprising a topsheet, a backsheet and an absorbent core disposed between the topsheet and the backsheet. The absorbent article may also include an ear disposed in one of the first or second waist regions and having a laminate. The laminate may include a first nonwoven and a second nonwoven and an elastomeric material sandwiched between said first and second nonwovens in an elasticized region; and a plurality of ultrasonic bonds. In addition, the laminate may include a first region and a second region, wherein each region has a Breathability Value of at least $1.0 \ m^3/m^2/min$ and wherein the Breathability Ratio of the first region to the second region is at least 1.1.

BRIEF DESCRIPTION OF THE DRAWINGS

FIG. 2 is a schematic plan view of an exemplary ear according to one nonlimiting embodiment of the present invention.

FIG. 3 is a schematic, exploded cross sectional view of an exemplary ear according to a nonlimiting embodiment of the present invention.

FIG. 4 is a schematic, exploded cross sectional view of an exemplary ear according to another nonlimiting embodiment of the present invention FIGS. 5-9 are schematic plan views of an exemplary ears according to nonlimiting embodiments of the present invention.

FIG. 10 is a schematic perspective view of a package in accordance with one embodiment of the present invention.

DETAILED DESCRIPTION OF THE INVENTION

Definitions

Figure 1:
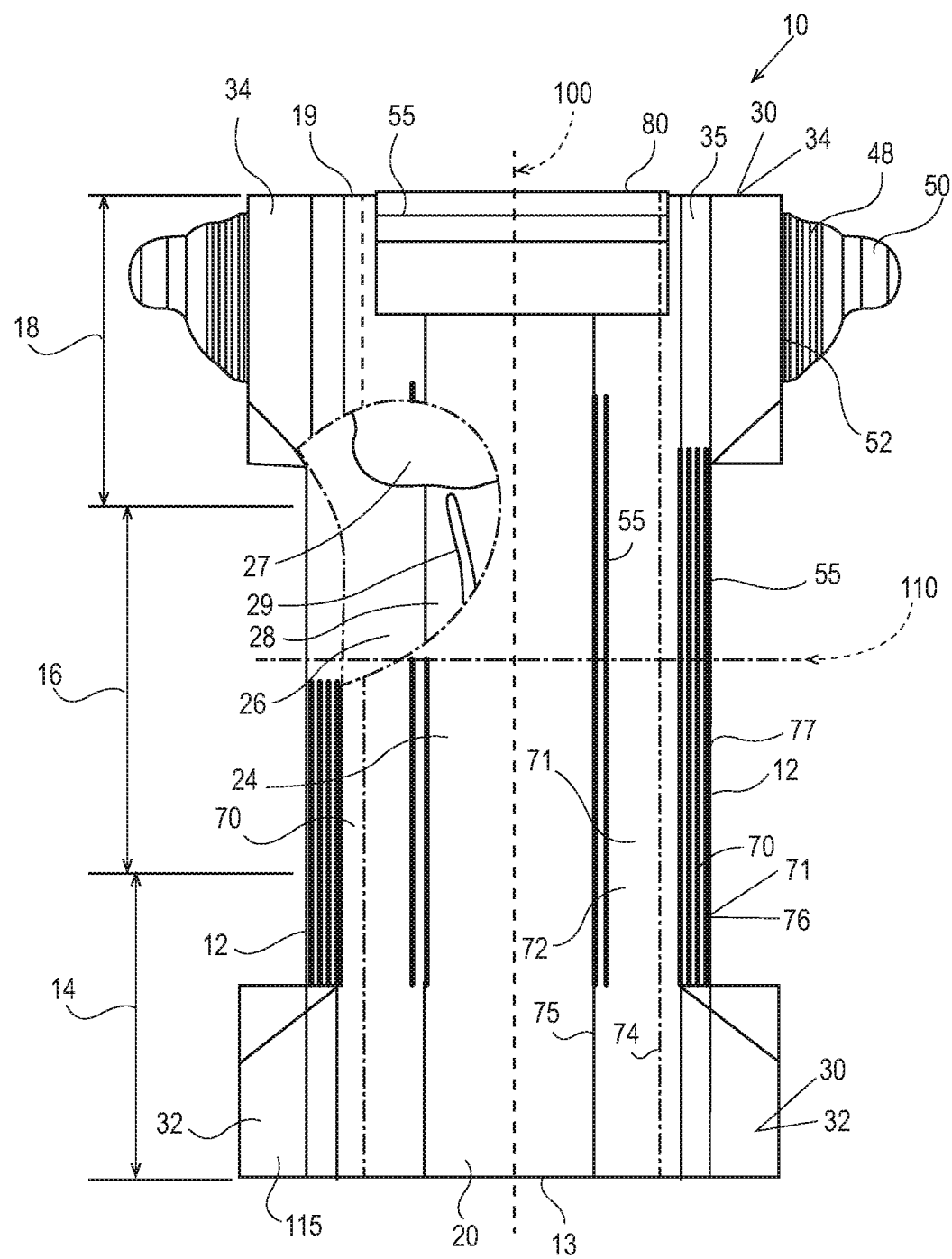
FIG. 1 is schematic plan view of an exemplary absorbent article according to one nonlimiting embodiment of the present invention. The absorbent article is shown in a flat, uncontracted state.

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Activation" is the mechanical deformation of a plastically extensible material that results in permanent elongation of the extensible material, or a portion of the extensible material, in the direction of activation in the X-Y plane of the material. For example, activation occurs when a web or portion of a web is subjected to a stress that causes the material to strain beyond the onset of plasticity, which may or may not include complete mechanical failure of the material or portion of the material. Activation of a laminate that includes an elastic material joined to a plastically extensible material typically results in permanent deformation of the plastic material, while the elastic material returns substantially to its original dimension. Activation processes are disclosed in U.S. Pat. Pub. No. 2013/0082418, U.S. Pat. Nos. 5,167,897 and 5,993,432.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Bond density" refers to bond frequency and/or aggregate bond coverage.

"Bond frequency" refers to the number of bonds per $cm^2$ as determined by the Bond Dimensions Test Method herein.

"Aggregate bond coverage" refers to the sum of the bond areas in a given region as determined by the Bond Dimension Test Method herein.

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal." "Longitudinally-extending" refers to components having a longitudinal dimension which is greater than said component's lateral dimension. "Longitudinally-extensible" refers to components that are extensible in the longitudinal direction.

"Lateral" refers to a direction running from a longitudinal edge to an opposing longitudinal edge of the article and generally at a right angle to the longitudinal direction. Directions within 45 degrees of the lateral direction are considered to be "lateral." "Laterally-extending" refers to components having a lateral dimension which is greater than said component's longitudinal dimension. "Laterally-extensible" refers to components that are extensible when stretched in the lateral direction.

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" means a sheet-like material wherein the length and width of the material far exceed the thickness of the material (e.g., 10×, 50×, or even 1000× or more). Films are typically liquid impermeable but may be configured to be breathable.

"Laminate" means two or more materials that are bonded to one another by any suitable method known in the art (e.g., adhesive bonding, thermal bonding, or high pressure bonding using non-heated or heated patterned roll).

"Nonwoven" means a porous, fibrous material made from continuous (long) filaments (fibers) and/or discontinuous (short) filaments (fibers) by processes such as, for example, spunbonding, meltblowing, airlaying, carding, coforming, hydroentangling, and the like. Nonwovens do not have a woven or knitted filament pattern. Nonwovens may be liquid permeable or impermeable.

"Relaxed" means the state of an element, material or component at rest with substantially no external force acting on the element, other than gravity.

"Elastic," "elastomeric," and "elastically extensible" mean the ability of a material to stretch by at least 100% without rupture or breakage at a given load, and upon release of the load the elastic material or component exhibits at least 70% recovery (i.e., has less than 30% set) in one of the directions as per the Hysteresis Test described herein. Stretch, sometimes referred to as strain, percent strain, engineering strain, draw ratio, or elongation, along with recovery and set may each be determined according to the Hysteresis Test described in more detail below. Materials that are not elastic are referred as inelastic.

"Extensible" means the ability to stretch or elongate, without rupture or breakage, by at least 50% as per step 5(a) in the Hysteresis Test herein (replacing the specified 100% strain with 50% strain).

"Design element" as used herein means a shape or combination of shapes that visually create a distinct and discrete component, regardless of the size or orientation of the component. A design element may be present in one or more patterns. A design element may be present one or more times within one pattern. In one nonlimiting example, the same design element is present twice in one pattern—the second instance of the design element is smaller than the first instance. One of skill in the art will recognize that alternative arrangements are also possible. Design elements may comprise insignia. Design elements and/or combinations of design elements may comprise letters, words and/or graphics such as flowers, butterflies, hearts, character representations and the like. Design elements may be formed from bonds, including the shape of one or more bond(s). Design elements and/or combinations of design elements may comprise instructional indicia providing guidance or instruction to the caregiver relative to placement and/or fit of the article about the wearer.

"Pattern" as used herein means a decorative or distinctive design, not necessarily repeating or imitative, including but not limited to the following: clustered, geometric, spotted, helical, swirl, arrayed, textured, spiral, cycle, contoured, laced, tessellated, starburst, lobed, blocks, pleated, concave, convex, braided, tapered, and combinations thereof. In some embodiments, the pattern includes one or more repeating design elements.

"Insignia" as used herein means objects, character representations, words, colors, shapes or other indicia that can be used to distinguish, identify or represent the manufacturer, retailer, distributor and/or brand of a product, including but not limited to trademarks, logos, emblems, symbols, designs, figures, fonts, lettering, crests or similar identifying marks.

Absorbent Article

FIG. 1 is a plan view of an exemplary, non-limiting embodiment of an absorbent article 10 of the present invention in a flat, uncontracted state. The body-facing surface 115 of the absorbent article 10 is facing the viewer. The absorbent article 10 includes a longitudinal centerline 100 and a lateral centerline 110.

The absorbent article 10 comprises a chassis 20. The absorbent article 10 and chassis 20 are shown to have a first waist region 14, a second waist region 18 opposed to the first waist region 14, and a crotch region 16 located between the first waist region 14 and the second waist region 18. The waist regions 14 and 18 generally comprise those portions of the absorbent article 10 which, when worn, encircle the waist of the wearer. The waist regions 14 and 18 may include elastic members 55 such that they gather about the waist of the wearer to provide improved fit and containment. The crotch region 16 is the portion of the absorbent article 10 which, when the absorbent article 10 is worn, is generally positioned between the legs of the wearer.

The outer periphery of the chassis 20 is defined by longitudinal edges 12 and waist edges (first waist edge 13 in first waist region 14 and second waist edge 19 in second waist region 18). The chassis 20 may have opposing longitudinal edges 12 that are oriented generally parallel to the longitudinal centerline 100. However, for better fit, longitudinal edges 12 may be curved or angled to produce, for example, an "hourglass" shape article when viewed in a plan view as shown in FIG. 1. The chassis 20 may have opposing lateral edges 13, 19 (i.e., the first waist edge 13 and second waist edge 19) that are oriented generally parallel to the lateral centerline 110.

The chassis 20 may comprise a liquid permeable topsheet 24, a backsheet 26, and an absorbent core 28 between the topsheet 24 and the backsheet 26. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In some embodiments, an acquisition-distribution system 27 is disposed between the topsheet 26 and the absorbent core 28.

In certain embodiments, the chassis 20 comprises the main structure of the absorbent article 10 with other features added to form the composite absorbent article structure.

While the topsheet 24, the backsheet 26, and the absorbent core 28 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306.

Topsheet:

The topsheet 24 is generally a portion of the absorbent article 10 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. One topsheet 24 useful herein is available from BBA Fiberweb, Brentwood, Tenn. as supplier code 055SLPV09U. The topsheet 24 may be apertured.

Any portion of the topsheet 24 may be coated with a lotion or skin care composition as is known in the art. Non-limiting examples of suitable lotions include those described in U.S. Pat. Nos. 5,607,760; 5,609,587; 5,635,191; and 5,643,588. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

Absorbent Core:

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In some embodiments, the absorbent core may comprise one or more channels 29, wherein said channels are substantially free of absorbent particulate polymer material. The channels 29 may extend longitudinally or laterally. The absorbent core may further comprise two or more channels. The channels may be straight, curvilinear, angled or any workable combination thereof. In one nonlimiting example, two channels are symmetrically disposed about the longitudinal axis.

Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316, and U.S. patent application Ser. Nos. 13/491,642 and 15/232,901.

Backsheet:

The backsheet 26 is generally positioned such that it may be at least a portion of the garment-facing surface 120 of the absorbent article 10. Backsheet 26 may be designed to prevent the exudates absorbed by and contained within the absorbent article 10 from soiling articles that may contact the absorbent article 10, such as bed sheets and undergarments. In certain embodiments, the backsheet 26 is substantially water-impermeable. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the absorbent article 10 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer. The backsheet 26 may comprise an outer cover and an inner layer. The outer cover may be made of a soft, non-woven material. The inner layer may be made of a substantially liquid-impermeable film, such as a polymeric film. The outer cover and an inner layer may be joined together by adhesive or any other suitable material or method. A particularly suitable outer cover is available from Corovin GmbH, Peine, Germany as supplier code A18AH0, and a particularly suitable inner layer is available from RKW Gronau GmbH, Gronau, Germany as supplier code PGBR4WPR. While a variety of backsheet configurations are contemplated herein, it would be obvious to those skilled in the art that various other changes and modifications can be made without departing from the spirit and scope of the invention.

Ears/Fasteners:

The absorbent article 10 may include one or more ears 30, including for example front ears 32 disposed in the first waist region and/or back ears 34 disposed in the second waist region. The ears 30 may be integral with the chassis or discrete elements joined to the chassis 20 at a chassis attachment bond 35, which may join one or more layers of the ear to the chassis. The ears 30 may be extensible or elastic. The ears 30 may be formed from one or more nonwoven webs, woven webs, knitted fabrics, polymeric and elastomeric films, apertured films, sponges, foams, scrims, or combinations and/or laminates of any the foregoing.

As illustrated in FIG. 2, ears may include a distal edge 36 and a proximate edge 38. The distal edge 36 is the free distal longitudinal edge of the ear. The proximate edge 38 is substantially opposed to the distal edge 36. The proximate edge 38 is joined to or overlapped with the chassis when the ear is joined to the chassis, or is the side defined by a line extending from longitudinal side 12 in the widest area of the crotch region and running parallel to the longitudinal centerline in the case of integral ears. Ears may further include a first lateral edge 40 and an opposing second lateral edge 42, and lateral centerline line 43 which is generally parallel to the article's lateral centerline 110. An ear may additional comprise a maximum width, W, extending between the distal edge and proximate edge and a length, Lv, extending between the first and second lateral edges. In some instances, the length may vary at portions along the width of the ear, as shown in FIG. 2. For instance, the ear may comprise a maximum length along its proximate edge 38 and slope or otherwise vary such that the ear comprises a minimum length on its distal edge 36. The ear further comprises a proximate side 380 which encompasses the portion of the ear extending outward of the proximate edge 38 by about 5 mm as measured parallel to the lateral centerline 43, and a distal side 360 which encompasses the portion of the ear extending inward the distal edge by about 5 mm as measured parallel to the lateral centerline 43.

In some embodiments, the ear 30 may include elastomers, such that the ear is stretchable. In certain embodiments, the ears 30 may be formed of a stretch laminate such as a nonwoven/elastomeric material laminate or a nonwoven/elastomeric material/nonwoven laminate, which also results in the ear being stretchable. The ear 30 may be laterally-extensible. In some embodiments, the ear is elastic when stretched in the lateral direction. In further embodiments, the ear 30 may extend more in the lateral direction than in the longitudinal direction. Alternatively, the ear may extend more in the longitudinal direction than in the lateral direction.

In some embodiments, the ear comprises a laminate of a first nonwoven 300 and an elastomeric layer 304. In certain embodiments illustrated in FIGS. 3-4, an ear comprises a first nonwoven 300, a second nonwoven 302 and an elastomeric layer 304. The elastomeric layer 304 may be sandwiched between the first and second nonwovens. Additional layers may be included (e.g., additional nonwovens, inelastic materials, elastic or extensible materials, etc.).

Any suitable nonwoven may be used in an ear 30. Suitable nonwovens may comprise a basis weight of at least about 8 gsm, or about 30 gsm or less, or about 22 gsm or less, or about 17 gsm or less, or from about 10 gsm to about 22 gsm, reciting for said range every 1 increment therein. In non-limiting examples, a nonwoven comprises a meltblown layer. Additionally or alternatively, a nonwoven may comprise spunbond layers. In a nonlimiting example, a nonwoven comprises two or more spunbond layers. In further nonlimiting examples, one or more nonwovens may comprise a SMS configuration. Alternatively, one or more of the nonwovens in the ear may be void of meltblown layers. While meltblown layers have been found to enhance bonding in ears requiring adhesive (given the meltblown layer's inhibition of the adhesive's diffusion through the porous nonwoven structure), meltblown layers often lack strength.

In some embodiments, a nonwoven consists essentially of spunbond layers. In some nonlimiting examples, both the first and the second nonwoven comprises at least 2 spunbond layers, or 3 or more spunbond layers.

Where the ear 30 comprises more than one nonwoven, the nonwovens may comprise the same basis weight or different basis weights. Likewise, the nonwovens may comprise the same layer configuration (e.g., SMS) or different layer configurations. Further, a nonwoven in the ear may comprise the same or different features of nonwovens in the backsheet, topsheet, leg gasketing system and/or waist feature.

The elastomeric layer 304 comprises one or more elastomeric materials which provide elasticity to at least a portion of the layer 304. Nonlimiting examples of elastomeric materials include film (e.g., polyurethane films, films derived from rubber and/or other polymeric materials), an elastomeric coating applied to another substrate (e.g., a hot melt elastomer, an elastomeric adhesive, printed elastomer or elastomer co-extruded to another substrate), elastomeric nonwovens, scrims, and the like. Elastomeric materials can be formed from elastomeric polymers including polymers comprising styrene derivatives, polyesters, polyurethanes, polyether amides, polyolefins, combinations thereof or any suitable known elastomers including but not limited to co-extruded VISTAMAXX®. Exemplary elastomers and/or elastomeric materials are disclosed in U.S. Pat. Nos. 8,618,350; 6,410,129; 7,819,853; 8,795,809; 7,806,883; 6,677,258 and U.S. Pat. Pub. No. 2009/0258210. Commercially available elastomeric materials include KRATON (styrenic block copolymer; available from the Kraton Chemical Company, Houston, Tex.), SEPTON (styrenic block copolymer; available from Kuraray America, Inc., New York, N.Y.), VECTOR (styrenic block copolymer; available from TSRC Dexco Chemical Company, Houston, Tex.), ESTANE (polyurethane; available from Lubrizol, Inc, Ohio), PEBAX (polyether block amide; available from Arkema Chemicals, Philadelphia, Pa.), HYTREL (polyester; available from DuPont, Wilmington, Del.), VISTAMAXX (homopolyolefins and random copolymers, and blends of random copolymers, available from EXXON Mobile, Spring, Tex.) and VERSIFY (homopolyolefins and random copolymers, and blends of random copolymers, available from Dow Chemical Company, Midland, Mich.).

In nonlimiting examples, the elastomeric layer 304 comprises a film. The film may comprise a single layer or multiple layers. The film may be laterally-extensible or may be elastic when stretched in the lateral direction. The film may be preactivated as disclosed, for example, in U.S. Pat. No. 9,533,067. The elastomeric layer may comprise a width, Y, as shown for example in FIG. 2. In some embodiments, Y is less than the width, W, of the ear 30 by at least about 10 mm. The elastomeric layer may have a longitudinal dimension that is the same as the ear 30 along with the width of the elastomeric layer, or a longitudinal dimension that is less than the longitudinal length of the ear at any point along with the width of the elastomeric layer. In some embodiments, the elastomeric layer may have a basis weight of from about 5 to about 150 gsm, or from about 10 to about 100 gsm, or less than about 150 gsm, reciting for each range every 5 gsm increment therein.

As also illustrated in FIG. 2, the ear 30 may comprise an elasticized region 306. The elasticized region 306 is generally defined by the perimeter of the elastomeric material 304. In the elastic region, the ear is elastically extensible. In some embodiments, the area of the elastic region comprises at least about 20% of, or from about 30% to about 100%, or about 80% or less of the total area of the ear, reciting for said range every 5% increment therein. In further embodiments, Y (i.e., the maximum width of the elastomeric layer) is at least about 20% of, or from about 25% to about 100%, or from about 35% to about 85%, or about 80% or less of the total width, W, of the ear, reciting for each range every 5% increment therein.

The ear may further comprise one or more inelastic regions. In certain embodiments, the ear 30 comprises a first inelastic region 308, which extends laterally outward from the proximate edge 38 and is adjacent to the elastic region 306 at a first elastomeric material edge 307. The ear may further include a second inelastic region 310, which may extend laterally inward from the distal side 36 and may be adjacent to the elastic region 306 at a second elastomeric material edge 309. The first and second inelastic regions may be made of the same material(s) or different materials.

In certain embodiments, the ear 30 comprises a gathered laminate 44, wherein one of the layers is strained to a greater degree than a remaining layer during lamination. In this way, the less extensible layer (i.e., the nonwoven 300, 302) will form gathers when the laminate 44 is in a relaxed state. In some embodiments, at least a portion of the elastomeric layer is strained while the nonwoven(s) are in a relaxed state during lamination. The elastomeric layer may be stretched one or more directions. Corrugations then form in the nonwoven layer(s) when the subsequently formed laminate 44 is in a relaxed state. In nonlimiting examples, the elastomeric layer is stretched in a direction corresponding with the lateral direction of the article. In other words, when the ear is joined to the chassis subsequent to lamination, the ear laminate will be oriented such that the ear is stretchable in the lateral direction of the article (i.e., the ear is laterally-extensible). In further nonlimiting examples, the ear is also stretchable in the longitudinal direction.

In some instances, the first and/or second elastomeric material edge is not stretched or is stretched by less than 10% during lamination, thereby providing one or more unstretched regions 37, 39 along said edge. In some embodiments, an unstretched region comprises a maximum lateral width of about 2 mm to about 12 mm, reciting for said range every 1 mm increment therein. The maximum lateral width of the unstretched region may be about 40% or less of the width of the elastomeric layer, Y. In further embodiments, the unstretched region may extend at least about 80% of the longitudinal length, $L_y$, of the ear where the region 37, 39 is present. The length and/or the width of the unstretched regions may vary. Where multiple unstretched regions exist, they may comprise the same or different dimensions. For example, FIG. 2 depicts two unstretched regions 37, 39 with different lengths (i.e., different from each other) and each region 37, 39 having varying lengths throughout their respective widths ($Z_1$, $Z_2$).

The absorbent article 10 may also include a fastening system 48. When fastened, the fastening system 48 interconnects the first waist region 16 and the rear waist region 18 resulting in a waist circumference that may encircle the wearer during wear of the absorbent article 10. The fastening system 48 may comprise a fastening elements 50 such as tape tabs, hook and loop fastening components, interlocking fasteners such as tabs & slots, buckles, buttons, snaps, and/or hermaphroditic fastening components, although any other known fastening means are generally acceptable. The absorbent article may further comprise a landing zone to which a fastening element can engage and/or a release tape that protects the fastening elements from insult prior to use. Some exemplary surface fastening systems are disclosed in U.S. Pat. Nos. 3,848,594; 4,662,875; 4,846,815; 4,894,060;

4,946,527; 5,151,092; and 5,221,274. An exemplary interlocking fastening system is disclosed in U.S. Pat. No. 6,432,098. In some embodiments, the fastening system 48 and/or the element 50 is foldable.

The fastening system 48 may be joined to any suitable portion of the article 10 by any suitable means. In some embodiments, the fastening system is joined to the ear 30 at a fastener attachment bond 52 as illustrated in FIGS. 3-4 for example. The fastening system may be joined to the ear between layers as shown in FIG. 4. The fastening system may be joined to the ear on an exterior surface of the ear as shown for example in FIG. 3. The fastening system may be joined to a body-facing surface of the ear or a garment facing surface. In one nonlimiting example, the fastening system 48 and/or fastening elements 50 are ultrasonically bonded to the ear 30. The fastening attachment bond 52 comprises a maximum length, measured parallel to the longitudinal centerline. The maximum length may be about 30 mm or less, or about 28 mm or less, or from about 20 mm to about 35 mm, reciting for said range every 1 mm increment therein. The fastening attachment bond may join the fastening system to one or more layers of the ear, as shown in FIGS. 3-4.

The fastening system 48 may be joined to ear at the distal side 360. The fastening system may be disposed in the second inelastic region 310 (see FIG. 3). In further embodiments, the fastening system 48 is joined in the elastic region 306 of the ear (see FIG. 4). The inventors have found that joining the fastening system to the ear in the elastic region 306 improves the overall strength of the ear/fastening system combination during use and/or application. Without being bound by theory, it is believed that breakage in ears formed from ultrasonically bonded laminates initially occurs in an inelastic region at the distal side 360 as the intact nonwoven resists the stretching of the elastomeric layer; and therefore, joining the fastening system within the elastic region 306 reduces the stress on the inelastic portion of the ear. In some embodiments, the fastening system 48 is joined in the elastic region such that it overlaps with the elastic region for a maximum lateral overlap distance of D as depicted in FIG. 4. In certain nonlimiting examples, D may be from about 0.05% to about 5%, or about 1% to about 5% of Y (i.e., the maximum width of the elastic region), reciting for each range every 0.02% increment therein.

In certain embodiments, the ear may comprise an Breathability Value of at least about 1 $m^3/m^2/min$, or from about 1 $m^3/m^2/min$ to about 125 $m^3/m^2/min$, or from about 2 $m^3/m^2/min$ to about 50 $m^3/m^2/min$ according to the Air Permeability Test Method herein, reciting for each range every 1 $m^3/m^2/min$ increment therein.

In some embodiments, the ear may be void of adhesive. In some nonlimiting examples, the ear comprises adhesive bond(s) only at the chassis attachment bond 35 and/or at the fastener attachment bond 52.

Figure 6:
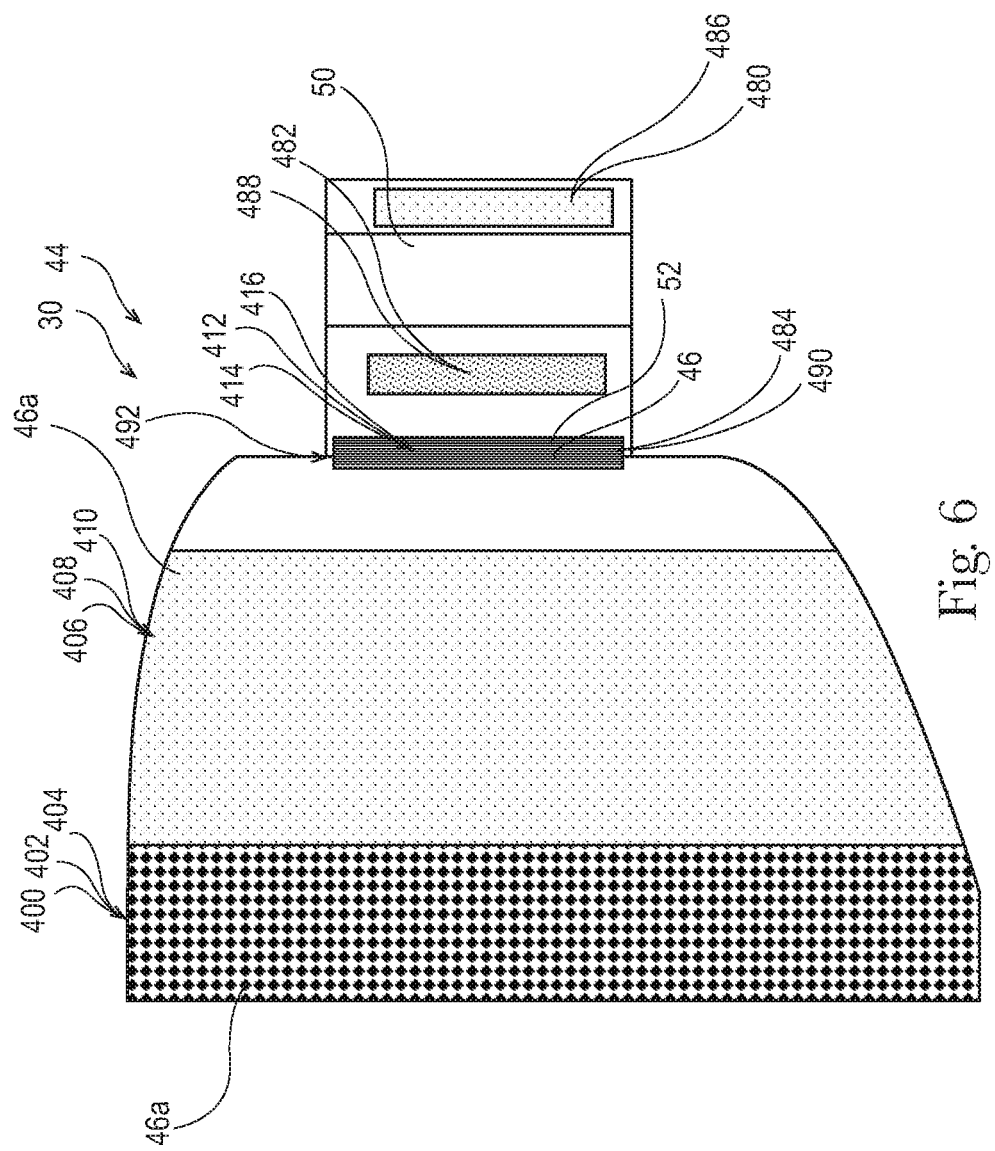

The laminate layers may be joined by one or more thermal bonds 46, such as ultrasonic bonds 46a, as illustrated in FIGS. 5-6, for example. The ultrasonic bonds may join the nonwoven layers through the elastomeric layer. The thermally bonded laminate may be formed by the process and/or equipment disclosed in commonly assigned U.S. patent application Ser. No. 62/419,515. Likewise, the chassis attachment bond 35 may comprise thermal bonds, which may consist of ultrasonic bonds. The chassis attachment bond 35 may bond one or more layers of the ear to the chassis as shown in FIGS. 3-4. The fastener attachment bond 52 may also comprise thermal bonds, which may consist of ultrasonic bonds. The bonds may be disposed in regions and/or patterns and can be used to provide customized properties in said region and/or pattern.

Returning to FIGS. 5-6, in embodiments, the ear comprises a first bonding region 400. The first bonding region may comprise thermal bonds 46 in a first plurality of bonds 402. In some embodiments, the thermal bonds consist of ultrasonic bonds 46a disposed in a first plurality of ultrasonic bonds 402. For purposes of this disclosure, a bonding region may be described as comprising ultrasonic bonds but other forms of thermal bonds are also within scope of this disclosure.

FIG. 5 illustrates the first bonding region outlined to show the periphery of the region (i.e., region shape) as created by the first plurality of ultrasonic bonds 402. The first plurality of ultrasonic bonds 402 may join one or more layers of the ear laminate. Additionally or alternatively, the first plurality of ultrasonic bonds 402 may join two or more layers of the ear to the fastening system 48 or to the chassis 20. Bonds 46 within the first plurality 402 may join the same layers of the ear or different layers of the ear. The first bonding region may be longitudinally-extending or laterally-extending. The first bonding region may extend the entire length of the ear where said first bonding region is present (as shown in FIG. 6) or may extend less than the full length of the ear where said bonding region is present (see FIG. 5). In some embodiments, the first bonding region may extend about 20% to about 80% of, or about 80% or less, or about 75% or less, or about 60% or less than the full length of the ear where the first region is present, reciting for said range every 10% increment therein. In this way, at a given lateral distance from the distal edge of the ear, the ear may comprise different bonding regions and/or the presence and absence of bonding regions at different longitudinal positions. In other words, the bonding and resulting properties created by bonding as described herein can be varied longitudinally. Additionally or alternatively, the first bonding region can be aligned with a feature of the ear or fastener or a certain position of said feature. In nonlimiting examples, the first bonding region is aligned such that a portion of the periphery of the first bonding region aligns with a waist edge, an edge of the fastening system, and/or a portion of the fastening system.

Further, the first plurality of bonds 402 may be disposed in a pattern 404 as shown in FIG. 6. Alternatively, the first plurality of bonds 402 may be disposed such that they form no discernible pattern as shown in FIG. 5.

The ear may further comprise a second bonding region 406, which includes a second plurality of thermal bonds 408. The second plurality of thermal bonds may comprise a second plurality of ultrasonic bonds 408. The second bonding region 406 may be adjacent to the first bonding region 400 or may be spaced apart from the first bonding region 400. The second plurality of ultrasonic bonds 408 may join two or more layers of the ear laminate. Additionally, the second plurality of ultrasonic bonds 408 may also join one or more layers of the ear to the fastening system 48 or to the chassis 20. The second plurality of bonds 408 may join the same layers as the first plurality or different layers. Bonds 46 within the second plurality 408 may join the same layers or different layers. The second bonding region may be longitudinally-extending or laterally-extending. The second bonding region may extend the entire length of the ear where said second region is present (as shown in FIG. 6) or may extend less than the full length of the ear where said second region is present (see FIG. 5). In some embodiments, the second bonding region may extend about 20% to about 80% of, or about 80% or less, or about 75% or less, or about 60% or less than the full length of the ear where the second region is present, reciting for said range every 10% increment therein. In this way, at a given lateral distance from the distal edge of the ear, the ear may comprise different bonding regions and/or the presence and absence of bonding regions at different longitudinal positions. In other words, the bonding and resulting properties created by bonding as described herein can be varied longitudinally. Additionally or alternatively, the second bonding region can be aligned with a feature of the ear or fastening system or a certain position of said feature. In nonlimiting examples, the second bonding region is aligned such that a portion of the periphery of the second bonding region aligns with a waist edge, an edge of the fastening system, and/or a portion of the fastening system.

Further, the second plurality of bonds 408 may be disposed in a second pattern 410 as illustrated in FIG. 6. In other embodiments, the second plurality of bonds 410 may be disposed in the first pattern. In other words, the two regions may comprise substantially the same pattern. Alternatively, the second plurality of bonds 408 may be disposed such that they form no discernible pattern as shown in FIG. 5.

Likewise, the ear may comprise additional bonding regions having thermal bonds which may be disposed in a pattern. For instance, the ear may include a third bonding region 412, having a third plurality of thermal bonds 414 which may be disposed in a third pattern 416 as is shown in FIG. 6 for example. The additional regions may have the same properties as the first or second bonding regions or have different properties. An additional bonding region, such as a third bonding region, may extend laterally or longitudinally, and may extend the full longitudinal length of the ear where said additional bonding region is present or less than the full length of the ear where said additional bonding region is present. In some embodiments, the additional bonding region may extend about 20% to about 80% of, or about 80% or less, or about 75% or less, or about 60% or less than the full length of the ear where said region is present, reciting for said range every 10% increment therein. In this way, at a given lateral distance from the distal edge of the ear, the ear may comprise different bonding regions and/or the presence and absence of bonding regions at different longitudinal positions. In other words, the bonding and resulting properties created by bonding as described herein can be varied longitudinally. Additionally or alternatively, an additional bonding region can be aligned with a feature of the ear or fastener or a certain position of said feature. In nonlimiting examples, the additional bonding region is aligned such that a portion of the periphery of the additional bonding region aligns with a waist edge, an edge of the fastening system, and/or a portion of the fastening system.

The first plurality of bonds 402 may comprise a first bond density. The second bonding plurality 408 may comprise a second bond density, different from the first bond density. In some embodiments, the first and second bond densities differ by bond frequency, as determined by the Bond Measurement Test Method herein. In further embodiments, the first and second bond densities differ by the aggregate bond coverage of their respective regions, as determined by the Bond Measurement Test Method herein. By way of nonlimiting example, the first bonding region may comprise a higher bond frequency than the second bond region as is schematically illustrated in FIG. 5 and/or the first bonding region may comprise a greater aggregate bond coverage than the second bond region. The first bond density may be at least 5% greater than the second bond density (i.e., 5% greater bond frequency and/or 5% greater aggregate bond coverage), or at least 10% greater, or from about 10% to about 90% greater, or from about 15% to about 85% greater, or from about 25% to about 75% greater than the second bond density, reciting for each range every 10% increment therein. In some embodiments, the first bonding region comprises a higher bond frequency than the second bonding region. Additionally or alternatively, the first bonding region may comprise a higher aggregate bond area than the second bonding region. Providing a higher bond density in a given bonding region allows for increased bond strength, reduced stress concentrations, increased modulus, different stretch level and/or greater breathability in said bonding region. Likewise, the ear may comprise a third bond density in the third bonding region 412, which may be the same as the first bonding region or the same as the second bonding region. Alternatively, the third bond density is greater than the second bond density or otherwise different from the first and/or second bond densities. It is also contemplated that two or more bond densities may be the same. In some embodiments, the bond densities of the first and second region are the same, but the bonding regions differ by the design elements; average spacing between bonds in the region; the sizes, shapes and/or orientation of the bonds in the regions; the aggregate bond area; and/or the overall shape of the bonding region (i.e., the perimeter of the region).

The first bonding region 400 may be disposed on the proximate side 380 of the ear such that minimum distance between the closest bond in the first plurality to the proximate edge 38 of the ear is no more than 5 mm, as measured parallel to the lateral centerline 43. In some embodiments, the chassis attachment bond 35 is at least partially disposed within the bonding region 400. In further nonlimiting examples, the first bonding region 400 is longitudinally-extending and at least partially disposed on the proximate side 380. By positioning the first bonding region having a higher bond density on the proximate side, the strength of ear laminate at the attachment area can be increased. This increased lamination strength may improve the transfer of forces from the chassis attachment bond to the ear, reducing stress on the bond site and/or stress concentrations in the laminate. Additionally or alternatively, by having a first bonding region with a first bond pattern disposed on the proximate side 38, the ear can be provided with unique visual characteristics in the area. By way of nonlimiting examples, the pattern 404 may comprise insignia, instructional indicia, garment-like patterns and/or other design elements which distinguish the proximate side from other portions of the ear as can be seen in FIG. 6.

In certain embodiments, a bonding region (e.g., first or third bonding region) may be disposed on the distal side 36 of the ear such that the minimum distance between the closest bond in the first plurality to the distal edge of the ear is no more than 5 mm or less, as measured parallel to the lateral centerline 43. In a nonlimiting example, the fastener attachment bond 52 is at least partially disposed in the said bonding region (illustrated in FIG. 6 as the third bonding region 412). By positioning a bonding region with a higher bond density on the distal side, the strength of the ear laminate at the attachment area can be increased, and said increased lamination strength may improve the transfer of forces from the fastener attachment bond to the fastener, reducing stress on the bond site and/or stress concentrations in the laminate. Additionally or alternatively, by having a bonding region with a bond pattern disposed on the distal side 360, the ear can be provided with unique visual characteristics in the area. By way of nonlimiting examples, the pattern, 416 may comprise insignia, instructional indicia, garment-like patterns and/or other design elements which distinguish the distal side from other portions of the ear as can be seen in FIG. 6.

The first bonding region may comprise a first pattern 404 and the second bonding region may comprise a second pattern 410. The first and second bond patterns may differ in various ways, including but not limited to the design elements; average spacing between bonds within the patterns; uniformity within the patterns; the sizes, shapes and/or orientation of the bonds within the patterns; the aggregate bond area within the patterns; and/or the overall pattern shape (i.e., the perimeter of the pattern). In embodiments that include a third bonding region, a third pattern 416 may differ from the first and/or the second bond pattern as well. The bonding regions may comprise different bond densities, or two or more of the bonding regions may comprise the same bond density while having different bond patterns. In nonlimiting examples, the first and second bond regions have the same bond density and the first and second bond patterns differ by the design elements; average spacing between bonds within the patterns; uniformity within the patterns; the sizes, shapes and/or orientation of the bonds within the patterns; the aggregate bond area within the patterns; and/or the overall shape (i.e., the perimeter of the pattern).

In some embodiments, the second pattern is at least partially disposed in the elasticized region 306. In some nonlimiting examples, the second bond pattern 410 comprises, on average, greater spacing between bonds within the pattern 410 than the spacing of between bonds of the first bond pattern 404. Greater spacing can emphasize certain properties of the ear. For instance, greater bond spacing in the elasticized region 306 can emphasize the corrugations produced in the elasticized region. Indeed, wider lateral spacing between bonds can create fewer but larger corrugations in a gathered laminate 44. In further embodiments, the second bond pattern 410 may comprise graphics.

Additionally or alternatively, a bonding region (e.g., the first or the third bonding region) can be used to emphasize the elasticized region, framing the region and indicating to the end user where the elasticized region is, as is shown in FIG. 7. This can be achieved by, for example, closer spacing between bonds, higher bond density, staggered patterns and/or graphics in areas adjacent to the elasticized region and/or in the unstretched region(s).

In certain embodiments, the first bonding region 400 may at least partially overlay at least one unstretched region 37, 39. The first bonding region may overlay at least a portion of the unstretched region for the full longitudinal length of said portion, or may overlay said portion for less than its full length. Increasing the bond density in an unstretched region may reduce stress concentrations on the elastomeric material caused during stretching and may enable the use of lower basis weight elastomeric materials, weaker elastomeric materials and/or less elastomeric material while maintaining sufficient laminate strength for the article 10. The increased bond density may also reduce risk of film tearing. In some embodiments, the unstretched region may be disposed within the first bonding region and comprise maximum width, $Z_1$, of from about 2 to about 6 mm, or from about 2 to about 4 mm, reciting for each range every 1 mm increment therein. In some embodiments, an additional unstretched region 39 is disposed in a third bonding region 412, which may have a higher bond density than the first and/or second bond density.

In certain embodiments, the orientation of one or more bonds in the first plurality 402 may differ from the orientation of one or more bonds in the second plurality 408 as shown in FIG. 8. By way of nonlimiting example, the majority of the bonds in the first plurality may be oriented 1-90° with respect to the ear centerline 43 and the majority of bonds in the second plurality may be oriented 91-180° with respect to the ear centerline 43, or vice versa. Any workable combination of different orientations is contemplated. Likewise, a third plurality of bonds can comprise a different orientation from the first and/or second pluralities.

In embodiments, the first bonding and second bonding regions each comprises a Breathability Value 1 $m^3/m^2/min$, or from about 1 $m^3/m^2/min$ to about 125 $m^3/m^2/min$ as determined by the Air Permeability Test Method herein, and the first bonding region comprises a Breathability Value that is greater than that of the second bonding region. In nonlimiting examples, the Breathability Ratio of the first bonding region to the second bonding region is at least 1.1. Additionally or alternatively, the bonding regions may differ in modulus, extensibility, strength, and/or appearance. In some nonlimiting examples, the modulus in the first bonding region is greater than the modulus in the second bonding region.

Any of the bonding regions may extend in the direction of stretch within the ear. In this way, the bonding region can be used to enhance the stretch profile of the ear. In some embodiments, one or more bonding regions are laterally-extending. In further embodiments, the bonding regions comprise a shape determined by the periphery created by the outermost bonds in the region. In nonlimiting examples, one or more bonding regions 400, 406, 412 can comprise a generally trapezoidal shape as is depicted in FIG. 9. By forming the bonding region in a trapezoidal shape, the modulus of the ear can be customized to create a better fit profile on the wearer. Further, the bonding regions and/or patterns may be used to create force, stretch, modulus profiles or other features described in U.S. Pat. Nos. 8,858, 523; 8,062,278; 8,491,557; 8,690,852 and 9,211,221.

Returning to FIG. 6, the fastener 48 may comprise thermal bonds, which may consist of ultrasonic bonds. The ultrasonic bonds may be disposed in one or more fastener bonding regions 480, 482, 484, any of which may have a bond pattern 486, 488, 490. In some nonlimiting examples, a fastener bond pattern 480 may match one or more bond patterns on the ear. For instance, a fastener bond pattern 480 may match the first bond pattern 404, or the second bond pattern 410 as shown in FIG. 6. Matching does not require patterns to be exactly the same; rather, the patterns may comprise substantially similar design elements, which may be rotated, mirrored, reduced in size, enlarged in size and/or altered in aspect ratio between the patterns and still be considered matching. In further nonlimiting examples, a fastener bonding pattern 484 differs from one or more bonding patterns on the ear. The patterns may differ in various ways, including but not limited to the design elements, average spacing between bonds within the patterns; uniformity within the patterns; the sizes, shapes and/or orientation of the bonds within the patterns; the aggregate bond area within the patterns; and/or the overall pattern shape (i.e., the perimeter of the pattern). The fastening system may overlap the distal side of the ear to form an overlapping region 492 as can be seen in FIG. 6. In some embodiments, the overlapping region comprises a bonding region 484. Said bonding region 484 may comprise a pattern 490 that differs from any of the bond patterns on the ear (404, 410, 416) and/or any of the bond patterns on the fastening system (486, 488). Alternatively, the overlapping region 492 may comprise a bonding region 484 having a pattern 490 that matches any of the remaining bond patterns on the ear and/or fastening system. The fastening system may comprise a Breathability Value of at least 1 $m^3/m^2/min$. In nonlimiting examples, the Breathability Ratio between a bonding region 400, 406, 412 on the ear and the fastener bonding region 480 is at least 1.1. Said fastener bonding region 480 may be disposed on the fastening system such that it does not overlap the ear laminate.

In addition, the ear may comprise one or more bonds formed by other bonding techniques that include but are not limited to adhesive bonding, mechanical bonding, pressure bonding, heat bonding and workable combinations thereof. These additional bonds may be used in conjunction with one or more ultrasonic bonding regions, or in separate areas of the ear. In some embodiments, at least a portion of the ear is activated by mechanical activation.

Leg Gasketing System

Returning to FIG. 1, the absorbent article 10 may comprise a leg gasketing system 70 attached to the chassis 20, which may comprise one or more cuffs 71. The leg gasketing system may comprise a pair of barrier leg cuffs 72. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs are delimited by a proximate edge joined directly or indirectly to the topsheet 24 and/or the backsheet 26 and a free terminal edge 75, which is intended to contact and form a seal with the wearer's skin. In some embodiments, the free terminal edge 75 comprises a folded edge. The barrier leg cuffs 72 extend at least partially between the front waist edge 13 and the rear waist edge 19 of the absorbent article on opposite sides of the longitudinal centerline 100 and are at least present in the crotch region. The barrier leg cuffs may be joined at the proximate edge with the chassis of the article by a bond which may be made by gluing, fusion bonding, or a combination of other suitable bonding processes.

The barrier leg cuffs may be integral with the topsheet 24 or the backsheet 26 or may be a separate material joined to the article's chassis. Each barrier leg cuff 72 may comprise one, two or more elastic elements 55 close to the free terminal edge 75 to provide a better seal.

In addition to the barrier leg cuffs 72, the article may comprise gasketing cuffs 76, which are joined to the chassis of the absorbent article, in particular to the topsheet 24 and/or the backsheet 26 and are placed externally relative to the barrier leg cuffs 72. The gasketing cuffs 76 may provide a better seal around the thighs of the wearer. A gasketing cuff may comprise a proximate edge and a free terminal edge 77. The free terminal edge 77 may comprise a folded edge. Each gasketing cuff may comprise one or more elastic elements 55 in the chassis of the absorbent article between the topsheet 24 and backsheet 26 in the area of the leg openings. All, or a portion of, the barrier leg cuffs and/or gasketing cuffs may be treated with a lotion or another skin care composition.

In further embodiments, the leg gasketing system comprises barrier leg cuffs that are integral with gasketing cuffs.

Suitable leg gasketing systems which may be part of the absorbent article are disclosed in U.S. patent applicaton Ser. Nos. 62/134,622, 14/077,708; U.S. Pat. Nos. 8,939,957; 3,860,003; 7,435,243; 8,062,279.

Elastic Waist Festure

The absorbent article 10 may comprise at least one elastic waist feature 80 that helps to provide improved fit and containment, as shown in FIG. 1. The elastic waist feature 80 is generally intended to expand and contract to dynamically fit the wearer's waist. Elasticized waist features include waistbands, waist cuffs having pockets formed from a portion of the waist feature 80 that is unattached from the chassis 20, and waist panels designed to fit securely about the abdomen of the wearer. Nonlimiting examples of elasticized waist features are disclosed in U.S. patent application Ser. Nos. 13/490,543; 14/533,472; and 62/134,622. Waist features 80 may be joined to the chassis 20 in the first waist region 14 and/or in the second waist region 16. The waist feature can be used in conjunction with the ear 30 to provide desirable stretch and flexibility for proper fit of the article on the wearer.

Package

The absorbent articles 10 of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

FIG. 10 illustrates an example package 1000 comprising a plurality of absorbent articles 1004. The package 1000 defines an interior space 1002 in which the plurality of absorbent articles 1004 are situated. The plurality of absorbent articles 1004 are arranged in one or more stacks 1006.

Combinations

While embodiments are described separately herein for brevity and clarity, combinations of the various embodiments are contemplated as exemplified below and are within the scope of the present disclosure.

A. An absorbent article comprising:
  a first waist region, a second waist region and a crotch region disposed between the first and second waist regions;
  a chassis comprising a topsheet, a backsheet and an absorbent core disposed between the topsheet and the backsheet; and an ear disposed in one of the first or second waist regions, the ear comprising:
  a proximate side and a distal side, a width and a length;
  an elasticized region; and
  a laminate comprising:
    a first nonwoven and a second nonwoven and an elastomeric material sandwiched between said first and second nonwovens in the elasticized region;
    a first bonding region comprising a first plurality of thermal bonds having a first bond density and optionally a first bond pattern, and
    a second bonding region comprising a second plurality of thermal bonds having a second bond density and optionally having a second bond pattern,
  wherein (i) the first bond density is greater than the second bond density or (ii) the first bond density is equal to the second bond density and at least one of the first plurality of bonds comprises a shape that is different from a shape of at least one of the second plurality of bonds.
B. The absorbent article of paragraph A wherein the first bond density is at least 5% greater than the second bond density.
C. The absorbent article of any of the preceding claims wherein the first bond pattern and the second bond pattern differ by design element(s) average bond spacing, pattern uniformity, bond size, bond shape, bond orientation, aggregate bond area, aggregate bond coverage, aggregate pattern shape and combinations thereof.
D. The absorbent article of paragraph C wherein the first and second bond patterns differ by bond spacing such that the second bond pattern comprises a greater average bond spacing than the first bond pattern.
E. The absorbent article of any of the preceding paragraphs wherein the second bonding region is at least partially disposed in the elasticized region.
F. The absorbent article of any of the preceding paragraphs wherein the first bonding region and the second bonding region are adjacent.
G. The absorbent article of any of the preceding paragraphs wherein the first bonding region is disposed on the proximate side.
H. The absorbent article of any of the preceding paragraphs wherein the ear further comprises a first inelastic region at least partially disposed at the proximate side.
I. The absorbent article of paragraph H further comprising a second inelastic region at least partially disposed at the distal side wherein the elasticized region is at least partially disposed between the first and second inelastic regions.
J. The absorbent article of any of the preceding paragraphs wherein the elasticized region comprises a first edge and a second edge wherein at least one of the first or second edges is disposed in the first bonding region.
K. The absorbent article of any of the preceding paragraphs further comprising a third bonding region comprising a third bond density, in particular wherein the third bond density is greater than the second bond density.
L. The absorbent article of paragraph K wherein the third bonding region is disposed at least partially along the distal side.
M. The absorbent article of paragraphs K or L wherein the third bonding region comprises a third pattern, and wherein said third pattern is different from the second pattern.
N. The absorbent article of any of the preceding paragraphs wherein the second pattern comprises graphics.
O. The absorbent article of any of the preceding paragraphs wherein the first bonding region and/or the second bonding region comprise a trapezoid shape.
P. The absorbent article of any of the preceding paragraphs wherein:
  a. the first bonding region extends about 80% or less of the length of the ear where the first bonding region is present; and/or
  b. the second bonding region extends about 80% or less of the length of the ear where the second bonding region is present.
Q. The absorbent article of any of the preceding paragraphs further comprising a fastening system comprising a fastener pattern of thermal bonds, wherein the first bond pattern matches the fastener pattern.
R. The absorbent article of paragraph Q wherein the fastening system is joined to the ear in overlapping relationship with at least a portion of the distal side to form an overlapping region; wherein the overlapping region comprises an additional pattern of thermal bonds and wherein the additional pattern differs from the first and/or fastener patterns by design element(s), average bond spacing, pattern uniformity, bond size, bond shape, bond orientation, aggregate bond area, aggregate bond coverage, aggregate pattern shape and combinations thereof.
S. The absorbent article of paragraphs Q or R wherein the fastener pattern is visible from a garment-facing side of the article.
T. The absorbent article of any of paragraphs Q-S wherein the fastener pattern is visible from the body-facing side of the article.
U. The absorbent article of any of the preceding paragraphs wherein the first bond pattern and/or the second bond pattern is visible from the body-facing side of the article.
V. The absorbent article of any of the preceding paragraphs wherein the first bond pattern and/or the second bond pattern is visible from the garment-facing side of the article.
W. The absorbent article of any of the preceding paragraphs further wherein the first region and the second bonding region each comprise a Breathability Value of at least 1.0 m$^3$/m$^2$/min and wherein the Breathability Ratio of the first bonding region to the second bonding region is at least 1.1.
X. The absorbent article of any of the preceding paragraphs wherein the first and/or second bonding region is laterally-extending.
Y The absorbent article of any of paragraphs A-W wherein the first and/or second bonding region is longitudinally-extending.
Z. The absorbent article of any of the preceding paragraphs wherein the ear comprises a discrete ear.
AA. The absorbent article of paragraph Z wherein the discrete ear is joined to the chassis in the first bonding region.
BB. The absorbent article of any of the preceding paragraphs wherein the ear is disposed in the second waist region.
CC. The absorbent article of any of the preceding paragraphs wherein the ear is laterally-extensible.
DD. The absorbent article of any of the preceding paragraphs wherein the first bond density and the second bond density differ by bond frequency.
EE. The absorbent article of any of the preceding paragraphs wherein the first and second bond densities differ by aggregate bond coverage.

FF. The absorbent article of any of the preceding paragraphs wherein any of the thermal bonds comprise ultrasonic bonds.
GG. The absorbent article of any of the preceding paragraphs wherein all of the thermal bonds comprise ultrasonic bonds.
HH. A package comprising a plurality of absorbent articles according to any of the preceding paragraphs wherein the package comprises an In-Bag Stack Height of less than about 110 mm as defined by the In-Bag Stack Height Test Method herein.

Test Methods

Bond Dimension Test Method

The Bond Dimension Test is used to measure bond density of the laminate in the various bonding regions. For purposes of this method, a bond is the intentional joining of two or more layers and is the deformed area caused during the bonding process (e.g., the reduced caliper at the site of bonding). It is recognized that in some cases, the deformed area may include one or more apertures.

Specimen Collection

1. Uniform pattern regions: To measure bond density of the bonding region having a uniform pattern, a square specimen of 1 cm² area is cut from the patterned bonded region of the laminate. Care should be taken to avoid collecting specimen from an adjacent region, if it is different. If specimen collection size of 1 cm² square is larger than the patterned region, the specimen is collected in the rectangle shape having a 1 cm² area: the shorter dimension of the patterned region forms one side of the rectangle and the other is selected such a way that rectangle area is 1 cm².

2. Other regions: To measure bond density of a bonding region without a uniform pattern, identify the plurality of bonds of interest and outline the resulting periphery as in FIG. 5. The specimen is collected by cutting along the periphery.

3. To the extent bonding regions are not identifiable, the ear may be segmented into three longitudinally extending regions: The first region has a width corresponding to the maximum width between the proximate edge of the ear and edge of the chassis bond closest to the distal edge of the ear. The second region has a width corresponding to the maximum width between the distal edge and the edge of the fastener attachment bond closest to the proximate edge of the ear. The third region has a width that extends between the first and second regions. Each region extends longitudinally for the length of the ear in their respective regions and the lengths may vary in the same manner as the ear's length varies in their respective regions.

Bond Frequency: Bond density by bond frequency is calculated by counting number of bonds on the specimen and dividing the number of bonds by the specimen's area. To the extent that specimen collection creates a partial bond within the specimen area, the partial bond is counted as a fraction equal to the fraction of the area of the bond included within the specimen relative to the area of the whole bond (i.e., the bond prior to cutting the specimen). Bond dimensions are measured to accuracy of 0.01 mm using a microscope and/or imaging software. The dimensions for each bond are used to calculate the bond area as per the mathematical area formula for the given shape of the bond. A total of five specimens are used, and an average bond density by bond frequency is calculated.

Aggregate Bond Coverage: Bond density by aggregate bond coverage is calculated by summing the bond areas for each bond in the specimen and dividing it by the specimen's area. Bond dimensions are measured to accuracy of 0.01 mm using a microscope and/or imaging software. The dimensions for each bond are used to calculate the bond area as per the mathematical area formula for the given shape of the bond. The area of partial bonds inside the specimen are also measured. All bond areas within the specimen are added to calculate aggregate bond area for the specimen and then the aggregate bond area is divided by the area of the specimen to determine aggregate bond coverage. A total of five specimen are used and an average bond density by aggregate bond coverage is calculated.

Hysteresis Test Method

The Hysteresis Test can be used to various specified strain values. The Hysteresis Test utilizes a commercial tensile tester (e.g., from Instron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The specimens are conditioned for 24 hours prior to testing.

The specimen is cut with a dimension of 10 mm in the intended stretch direction of the ear X 25.4 mm in the direction perpendicular to the intended stretch direction of the ear. A specimen is collected from either an inelastic region or from an elastic region.

Test Protocol

1. Select the appropriate grips and load cell. The grips must have flat surfaces and must be wide enough to grasp the specimen along its full width. Also, the grips should provide adequate force and suitable surface to ensure that the specimen does not slip during testing. The load cell is selected so that the tensile response from the specimen tested is between 25% and 75% of the capacity of the load cell used.

2. Calibrate the tester according to the manufacturer's instructions.

3. Set the distance between the grips (gauge length) at 7 mm.

4. Place the specimen in the flat surfaces of the grips such that the uniform width lies along a direction perpendicular to the gauge length direction. Secure the specimen in the upper grip, let the specimen hang slack, then close the lower grip. Set the slack preload at 5 gram/force. This means that the data collection starts when the slack is removed (at a constant crosshead speed of 13 mm/min) with a force of 5 gram force. Strain is calculated based on the adjusted gauge length ($l_{ini}$), which is the length of the specimen in between the grips of the tensile tester at a force of 5 gram force. This adjusted gauge length is taken as the initial specimen length, and it corresponds to a strain of 0%. Percent strain at any point in the test is defined as the change in length relative to the adjusted gauge length, divided by the adjusted gauge length, multiplied by 100.

5(a) First cycle loading: Pull the specimen to the 100% strain at a constant cross head speed of 70 mm/min. Report the stretched specimen length between the grips as $l_{max}$.

5(b) First cycle unloading: Hold the specimen at the 100% strain for 30 seconds and then return the crosshead to its starting position (0% strain or initial sample length, $l_{ini}$) at a constant cross head speed of 70 mm/min. Hold the specimen in the unstrained state for 1 minute.

5(c) Second cycle loading: Pull the specimen to the 100% strain at a constant cross head speed of 70 mm/min.

5(d) Second cycle unload: Next, hold the specimen at the 100% strain for 30 seconds and then return the crosshead to its starting position (i.e. 0% strain) at a constant cross head speed of 70 mm/min.

A computer data system records the force exerted on the sample during the test as a function of applied strain. From the resulting data generated, the following quantities are reported.

i. Length of specimen between the grips at a slack preload of 5 gram-force ($l_{ini}$) to the nearest 0.001 mm.

ii. Length of specimen between the grips on first cycle at the 100% strain ($l_{max}$) to the nearest 0.001 mm.

iii. Length of specimen between the grips at a second cycle load force of 7 gram-force ($l_{ext}$) to the nearest 0.001 mm.

iv. % Set, which is defined as $(l_{ext}-l_{ini})/(l_{max}-l_{ini})*100\%$ to the nearest 0.01%. The testing is repeated for six separate samples and the average and standard deviation reported.

Air Permeability Test Method

The air permeability of an ear laminate or substrate (e.g., film, nonwoven, or article component) is determined by measuring the flow rate of standard conditioned air through a test specimen driven by a specified pressure drop. This test is particularly suited to materials having relatively high permeability to gases, such as nonwovens, apertured ear laminates and the like. ASTM D737 is used, modified as follows.

A TexTest FX 3300 instrument or equivalent is used, available from Textest AG, Switzerland, or from Advanced Testing Instruments ATI in Spartanburg S.C., USA. The procedures described in the Operating Instructions for the TEXTEST FX 3300 Air Permeability Tester manual for the Air Tightness Test and the Function and Calibration Check are followed. If a different instrument is used, similar provisions for air tightness and calibration are made according to the manufacturer's instructions.

The specimen is tested while in a relaxed state.

The test pressure drop is set to 500 Pascal and the 1 cm² area test head (model FX 3300-5) or equivalent is used. The result is recorded to three significant digits. The average of 5 specimens is calculated and reported as the Breathability Value ($m^3/m^2$/min).

To determine a Breathability Ratio between two regions, the Breathability Value of a region (i) is divided by the Breathability Value of the comparative region (ii): $BV_i/BV_{ii}$=Breathability Ratio.

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 10). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
a first waist region, a second waist region and a crotch region disposed between the first and second waist regions;
a chassis comprising a topsheet, a backsheet and an absorbent core disposed between the topsheet and the backsheet; and
an ear disposed in one of the first or second waist regions, the ear comprising:
a proximate side and a distal side, a width and a length;
a first inelastic region;
a second inelastic region;
an elasticized region disposed between the first inelastic region and the second inelastic region; and a laminate comprising:
   a first nonwoven and a second nonwoven and an elastomeric material sandwiched between said first and second nonwovens in the elasticized region;
   a first bonding region comprising a first plurality of ultrasonic bonds having a first bond density and a first bond pattern, wherein the first bonding region is disposed on the first inelastic region;
   a second bonding region comprising a second plurality of ultrasonic bonds having a second bond density and a second bond pattern, wherein the second bonding region is partially disposed on the elasticized region; and
   a third bonding region spaced from the second bonding region and comprising a third plurality of ultrasonic bonds having a third bond density, wherein the third bonding region is disposed on the second inelastic region, and
      wherein the first bond density and the third bond density are greater than the second bond density and wherein the second plurality is disposed between the first and the third pluralities, wherein the first bond density and the third bond density are different, wherein each of the first, second and third bond density are determined by bond frequency and/or aggregate bond coverage, and wherein the first bonding region and the second bonding region comprise different orientations and wherein the second bond pattern comprises a greater average bond spacing than the first bond pattern; and
   a fastening system extending from the distal side of the ear, wherein a fastener attachment bond attaches the fastening system to the second inelastic region, and wherein a portion of the fastener attachment bond overlaps a portion of the third bonding region.

2. The absorbent article of claim 1 wherein the first bond density is at least 5% greater than the second bond density.

3. The absorbent article of claim 1 wherein the first and second bond densities are determined solely by bond frequency.

4. The absorbent article of claim 1 wherein the first bond density and the second bond density are determined solely by aggregate bond coverage.

5. The absorbent article of claim 1 wherein the first bonding region and the second bonding region are adjacent.

6. The absorbent article of claim 1 wherein the first bonding region is disposed on the proximate side.

7. The absorbent article of claim 1 wherein the first inelastic region is at least partially disposed at the proximate side.

8. The absorbent article of claim 7 wherein the second inelastic region is at least partially disposed at the distal side.

9. The absorbent article of claim 8 wherein the elasticized region comprises a first edge and a second edge wherein at least one of the first or second edges is disposed in the first bonding region.

10. The absorbent article of claim 1 wherein the first bonding region extends the length of the ear along a lateral width where the first bonding region is present.

11. The absorbent article of claim 1 wherein the second bonding region extends the length of the ear along a lateral width where the second bonding region is present.

12. An absorbent article comprising:
a first waist region, a second waist region and a crotch region disposed between the first and second waist regions;
a chassis comprising a topsheet, a backsheet and an absorbent core disposed between the topsheet and the backsheet; and
an ear disposed in one of the first or second waist regions, wherein the ear is laterally-extensible and comprises:
   a proximate side and a distal side;
   an inelastic region and an elasticized region;
   a laminate comprising a first nonwoven and a second nonwoven and an elastomeric material sandwiched between said first and second nonwovens in the elasticized region, the laminate comprising a first pattern of ultrasonic bonds configured to join one or more layers of the laminate of the ear; and
   a fastening system joined to the ear in overlapping relationship with at least a portion of the distal side to form an overlapping region;
   the fastening system comprising a fastener pattern of ultrasonic bonds, wherein the first pattern matches the fastener pattern and is not configured to fasten to the fastening system, wherein the fastener pattern is disposed outside of the overlapping region and wherein a Breathability Ratio between the first pattern and the fastener pattern is at least 1.1.

13. An absorbent article comprising:
a lateral direction and a longitudinal direction;
a first waist region, a second waist region and a crotch region disposed between the first and second waist regions;
a chassis comprising a topsheet, a backsheet and an absorbent core disposed between the topsheet and the backsheet; and
an ear disposed in one of the first or second waist regions, the ear comprising:
   an inelastic region;
   an elasticized region adjacent to the inelastic region; and
   a laminate comprising:
      a first nonwoven and a second nonwoven and an elastomeric material sandwiched between said first and second nonwovens in the elasticized region;
      a first bonding region comprising a first plurality of ultrasonic bonds joining a first set of layers of the laminate and having a first bond density, and wherein the first bonding region is laterally-extending and disposed on the inelastic region; and
      a second bonding region disposed on the elasticized region, the second bonding region comprising a second plurality of ultrasonic bonds joining a second set of layers of the laminate different from the first set of layers and having a second bond density, wherein the first bond density differs from the second bond density; and
      wherein the combination of the first plurality of ultrasonic bonds and the second plurality of ultrasonic bonds comprise a laterally-extending trapezoidal shape, such that said laterally-extending trapezoidal shape comprises a lateral dimension that is greater than its longitudinal dimension.

* * * * *